US012758186B2

(12) United States Patent
Rahardja et al.

(10) Patent No.: US 12,758,186 B2
(45) Date of Patent: Oct. 13, 2026

(54) DUAL FUNCTION COOLING AND CHARGING UNIT FOR AN ULTRASOUND IMAGING APPARATUS, AND RELATED ULTRASOUND SYSTEMS

(71) Applicant: Clarius Mobile Health Corp., Vancouver (CA)

(72) Inventors: Daniel Rahardja, Burnaby (CA); Binda Zhang, Surrey (CA)

(73) Assignee: Clarius Mobile Health Corp., Vancouver (CA)

( * ) Notice: Subject to any disclaimer, the term of this patent is extended or adjusted under 35 U.S.C. 154(b) by 63 days.

(21) Appl. No.: 18/669,481

(22) Filed: May 20, 2024

(65) Prior Publication Data

US 2024/0341727 A1 Oct. 17, 2024

Related U.S. Application Data

(63) Continuation of application No. 17/576,988, filed on Jan. 16, 2022, now Pat. No. 11,986,347.

(51) Int. Cl.
*A61B 8/00* (2006.01)

(52) U.S. Cl.
CPC .......... *A61B 8/4433* (2013.01); *A61B 8/4472* (2013.01); *A61B 8/546* (2013.01); *A61B 8/56* (2013.01)

(58) Field of Classification Search
CPC ..... A61B 8/4433; A61B 8/4472; A61B 8/546; A61B 8/56
See application file for complete search history.

(56) References Cited

U.S. PATENT DOCUMENTS

| | | | |
|---|---|---|---|
| 5,560,362 | A | 10/1996 | Sliwa, Jr. et al. |
| 5,961,465 | A | 10/1999 | Kelly, Jr. et al. |
| 6,362,958 | B1 | 3/2002 | Yu et al. |
| 6,542,846 | B1 | 4/2003 | Miller et al. |
| 6,666,860 | B1 | 12/2003 | Takashashi |
| 6,709,392 | B1 | 3/2004 | Salgo et al. |
| 6,795,314 | B1 | 9/2004 | Arbogast et al. |
| 6,980,419 | B2 | 12/2005 | Smith et al. |
| 7,948,754 | B2 | 5/2011 | Huang |
| 7,998,072 | B2 | 8/2011 | Phelps et al. |

(Continued)

FOREIGN PATENT DOCUMENTS

JP 201008861 A 4/2010

OTHER PUBLICATIONS

English translation of foreign patent JP 2010088610 by Miyajima et al. 2010. Retrieved from Google Patents on Jan. 21, 2022.

(Continued)

*Primary Examiner* — Dixomara Vargas
(74) *Attorney, Agent, or Firm* — Julian Ho; Susan Ben-Oliel

(57) ABSTRACT

An ultrasound imaging system comprises an ultrasound imaging apparatus operable to acquire ultrasound image data and comprising a power accepting interface; and a dual function charging and cooling unit configured to detachably couple to the ultrasound imaging apparatus; wherein the dual function charging and cooling unit comprises i) a power conveying element to convey power to the ultrasound imaging apparatus and ii) an active cooling element for removing heat from the ultrasound imaging apparatus.

19 Claims, 12 Drawing Sheets

(56) References Cited

U.S. PATENT DOCUMENTS

| | | | | |
|---|---|---|---|---|
| 8,143,898 | B1 | 3/2012 | Markoff et al. | |
| 8,409,101 | B2 * | 4/2013 | Hongou | G10K 11/004 600/459 |
| 8,475,375 | B2 | 7/2013 | Smith et al. | |
| 10,206,658 | B2 * | 2/2019 | Lee | H02J 7/0044 |
| 11,083,439 | B2 * | 8/2021 | Chan | A61B 8/546 |
| 11,986,347 | B2 | 5/2024 | Rahardja et al. | |
| 2004/0002655 | A1 | 1/2004 | Bolorforosh et al. | |
| 2004/0073113 | A1 | 4/2004 | Salgo et al. | |
| 2004/0179332 | A1 | 9/2004 | Smith et al. | |
| 2005/0075573 | A1 | 4/2005 | Park et al. | |
| 2005/0117706 | A1 | 6/2005 | Powell | |
| 2005/0148878 | A1 | 7/2005 | Phelps et al. | |
| 2006/0082966 | A1 | 4/2006 | Lev et al. | |
| 2006/0100513 | A1 | 5/2006 | Hashimoto | |
| 2006/0191344 | A1 | 8/2006 | Hashimoto | |
| 2008/0146924 | A1 | 6/2008 | Smith et al. | |
| 2009/0261804 | A1 | 10/2009 | McKenna et al. | |
| 2010/0331702 | A1 * | 12/2010 | Hongou | A61B 8/546 600/459 |
| 2011/0096497 | A1 | 4/2011 | Huang | |
| 2012/0116363 | A1 * | 5/2012 | Houser | G16H 20/40 606/1 |
| 2016/0077059 | A1 | 3/2016 | Chung et al. | |
| 2016/0242747 | A1 | 8/2016 | Siedenburg et al. | |
| 2017/0020490 | A1 | 1/2017 | Ryu et al. | |
| 2017/0043189 | A1 | 2/2017 | Stoddard et al. | |
| 2017/0172542 | A1 * | 6/2017 | Lee | A61B 8/546 |
| 2018/0125461 | A1 * | 5/2018 | Clark | A61B 8/4444 |
| 2018/0344294 | A1 * | 12/2018 | Chan | A61B 8/546 |
| 2019/0290239 | A1 * | 9/2019 | Yim | A61B 8/469 |
| 2020/0268393 | A1 * | 8/2020 | Venturini | A61B 17/320068 |
| 2020/0297316 | A1 * | 9/2020 | Mclaughlin | A61B 8/14 |
| 2021/0387237 | A1 * | 12/2021 | Leighton | B05B 1/083 |
| 2023/0225706 | A1 | 7/2023 | Rahardja et al. | |

OTHER PUBLICATIONS

What is Pogo Pin? by Zhenghe Jun. 1, 2021. https://pogopin.net/what-is-pogo-pin/.

USB. 2022 Sharpened Productions. https://techterms.com/definition/usb.

USB Type A Connector: Everything You Need to Know. Chris Hoffman. How-To Geek. Sep. 18, 2020. https://www.howtogeek.com/690160/usb-type-a-connector-everything-you-need-to-know/.

* cited by examiner

DUAL FUNCTION COOLING AND CHARGING UNIT FOR AN ULTRASOUND IMAGING APPARATUS, AND RELATED ULTRASOUND SYSTEMS

CROSS-REFERENCE TO RELATED APPLICATION

This application is a continuation of U.S. patent application Ser. No. 17/576,988 entitled "DUAL FUNCTION COOLING AND CHARGING UNIT FOR AN ULTRASOUND IMAGING APPARATUS, AND RELATED ULTRASOUND SYSTEMS" filed Jan. 16, 2022, the entire contents of which are incorporated herein by reference.

FIELD OF THE INVENTION

The present disclosure relates generally to ultrasound imaging apparatus, and in particular, a dual function charging and cooling unit for an ultrasound imaging apparatus.

BACKGROUND OF THE INVENTION

Ultrasound imaging systems may generate heat during operation. For example, heat may be generated from the transducer elements in a transducer array when they are activated to transmit ultrasound signals. Also, heat may be generated by integrated circuits (ICs) that drive the transducer array and process imaging data.

When imaging tissue, ultrasound probes (also called ultrasound transducers) are typically placed against the skin of a patient. To prevent patient injury or discomfort due to the probe head having overly high temperatures, there exist regulations that require surfaces of an ultrasound probe to not exceed certain predetermined temperatures while scanning a patient (e.g. International Electrotechnical Commission (IEC) standard 60601 requires external surfaces of an ultrasound probe to not exceed 48° C. in certain conditions).

There are traditional methods of dissipating heat from an ultrasound imaging apparatus. For example, in a traditional wired ultrasound system, heat may be channeled into and through the cable so that it can be dissipated from the cable and/or through the processing body. Heat may also traditionally be dissipated through conduction to the operator and to the patient, and/or through convection to the air. However, during lengthy periods of continuous scanning, these traditional heat mechanisms may not be sufficient.

In addition to adequate heat management, several other considerations may influence the design and operation of an ultrasound imaging apparatus including ergonomics, battery life, and cleaning.

For example, in a wireless ultrasound imaging apparatus, it may be desirable to minimize the size and weight of the device; maximize operating time; and/or enable simple, quick, effective cleaning. A sealed and/or water-resistant enclosure may, for example, enable easier cleaning and sterilization, and/or operation in wet environments. Some traditional wireless ultrasound systems include internal fans or other active cooling elements to increase heat dissipation. However, such traditional systems also typically include slits or vents in the housing to allow airflow caused by the fan. Such slits or vents may make it difficult to clean the ultrasound system without exposing the internal fan or electronics to cleaning fluid that may cause damage to those components.

As an additional consideration, as the sizes of newer wireless ultrasound imaging devices have been steadily decreasing due to the enhanced power and miniaturisation of integrated circuits, there is less room to dissipate heat generated during scanning and use. In the quest to reduce the size and weight of newer wireless ultrasound imaging devices, instead of comprising a removable and rechargeable batteries there are now provided a fixed in place rechargeable batteries which require frequent charging for extended usage of the ultrasound imaging devices.

There is thus a need for improved cooling mechanisms for a variety of ultrasound imaging apparatuses. The embodiments discussed herein may address and/or ameliorate at least some of the aforementioned design considerations identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which.

DETAILED DESCRIPTION OF THE INVENTION

A. Glossary

Figure 1:
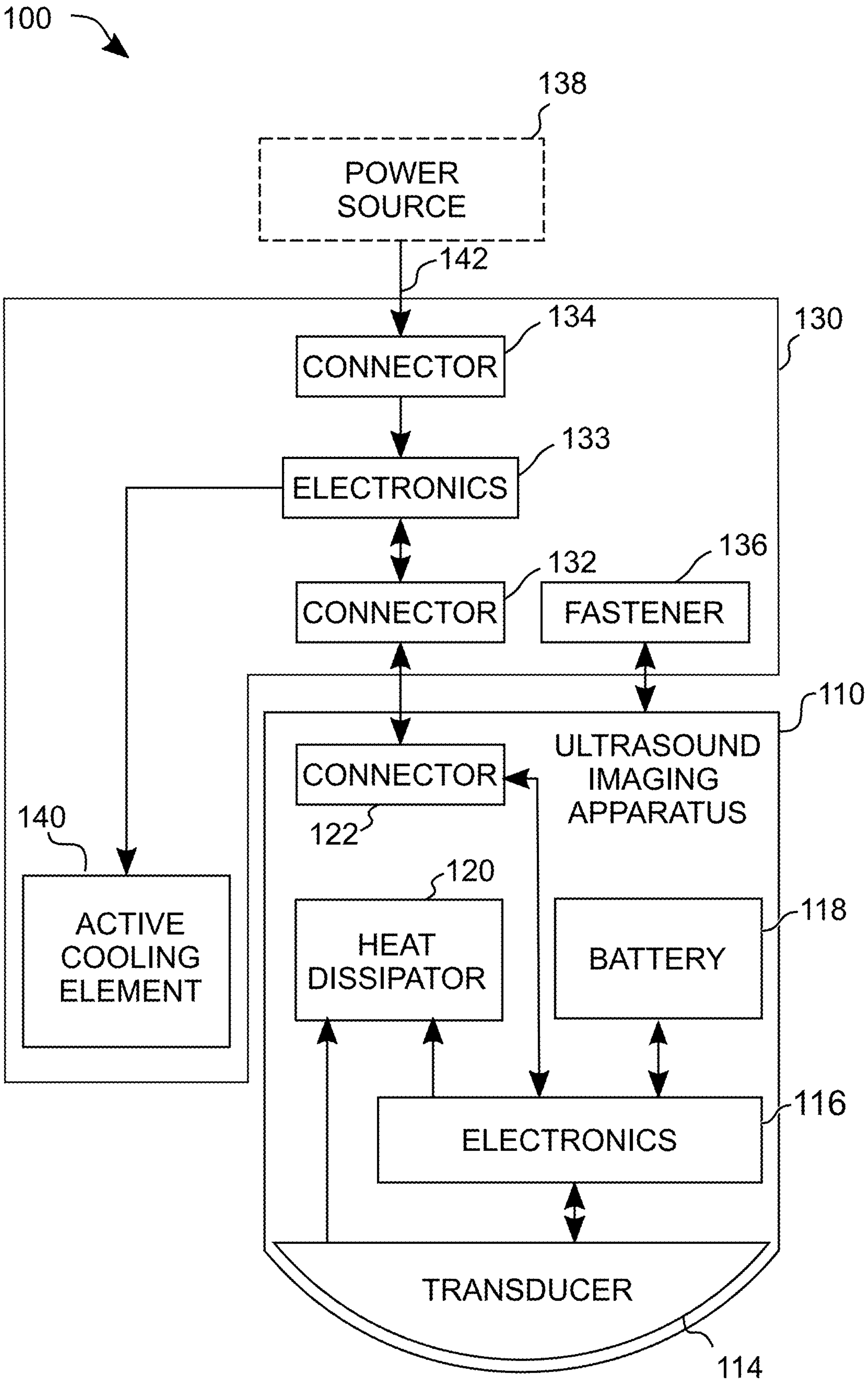
FIG. 1 shows a schematic representation of an ultrasound system, in accordance with at least one embodiment of the present invention.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as used in cloud computing or local virtualization, which are ultimately grounded in physical processors.

The term "module" can refer to any component in this invention and to any or all of the features of the invention without limitation. A module may be a software, firmware or hardware module, and may be located, for example, in the ultrasound scanner, in the dual function charging and cooling unit or in any associated charging dock.

The term "system" when used herein, and not otherwise qualified, refers to a system comprising two core components: an ultrasound imaging device and a removably attachable/detachable dual function charging and cooling unit. In some cases the system is referred to as the "two units" meaning the ultrasound imaging device and a removably attachable/detachable dual function charging and cooling unit. In some embodiments, the system may additionally comprise a detachable power cord for mating with the dual function charging and cooling unit and for conveying power to the ultrasound imaging device, when the dual function charging and cooling unit is coupled to the ultrasound imaging device. In some embodiments, the system may additionally comprise a detachable power cord for mating with the dual function charging and cooling unit to recharge a battery within the dual function charging and cooling unit.

The term "ultrasound imaging apparatus" when used herein, and not otherwise qualified may be used interchangeably with various other terms, such as, for example, ultrasound scanner, ultrasound transducer, ultrasound imaging device, scanner or ultrasound image capturing device.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

B. Exemplary Embodiments

In a first broad aspect of the present disclosure, there is provided an ultrasound imaging system, comprising an ultrasound imaging apparatus operable to acquire ultrasound image data and comprising a power accepting interface and a dual function charging and cooling unit configured to detachably couple to the ultrasound imaging apparatus, wherein the dual function charging and cooling unit comprises i) a power conveying element to convey power to the ultrasound imaging apparatus and ii) an active cooling element for removing heat from the ultrasound imaging apparatus when coupled thereto.

In some embodiments, the dual function charging and cooling unit comprises a power port for mating with a detachable power cord and wherein the power conveying element conveys power to the power accepting interface to power the ultrasound imaging apparatus when the dual function charging and cooling unit is coupled to the ultrasound imaging apparatus.

In some embodiments, the dual function charging and cooling unit comprises an in unit battery and the power conveying element conveys power to the power accepting interface to power the ultrasound imaging apparatus when the dual function charging and cooling unit is coupled to the ultrasound imaging apparatus.

In some embodiments, the power conveying element conveys power wirelessly to the power accepting interface, to power the ultrasound imaging apparatus, when the dual function charging and cooling unit is coupled to the ultrasound imaging apparatus.

In some embodiments, the power conveying element conveys power to the power accepting interface, to power the ultrasound imaging apparatus and in turn the ultrasound imaging apparatus powers the operation of the active cooling element within the dual function charging and cooling unit, when the ultrasound imaging apparatus and the dual function charging and cooling unit are coupled.

In some embodiments, the power accepting interface of the ultrasound imaging apparatus comprises an apparatus electronic connection point and the dual function charging and cooling unit comprises a corresponding unit electronic connection point for mating with the apparatus electronic connection point: i) to convey power to the ultrasound imaging apparatus; and in some embodiments, ii) to convey operating power from the ultrasound imaging apparatus to the dual function charging and cooling unit.

In some embodiments, the ultrasound imaging apparatus includes an external surface and the dual function charging and cooling unit comprises an active cooling element (for example, a fan), and said active cooling element is configured to direct air onto and/or from said external surface.

In some embodiments, the dual function charging and cooling unit comprises at least one attachment means to enable attachable/detachable coupling to the ultrasound imaging apparatus. In some embodiments, the attachment means is formed with mating components on a housing of the dual function charging and cooling unit and on a surface of the ultrasound imaging apparatus. In some embodiments, the attachment means comprises one or more protuberances or protrusions on an interior surface of a housing of the dual function charging and cooling unit which are insertable into apertures or dimples or receptacles on a surface of the ultrasound imaging apparatus. In some embodiments, the attachment means comprises includes at least one clip or fastener portion to provide the detachable coupling. In some embodiments, the dual function charging and cooling unit is coupled to the ultrasound imaging apparatus using magnetic force. In some embodiments, the dual function charging and cooling unit comprises a housing and said housing includes at least one magnet for performing the detachable coupling and wherein a body of the ultrasound imaging apparatus includes a magnetic material for mating with said at least one magnet. The present invention is not intended to be limited to any one mode of removable coupling, as there are a variety of simple and efficient ways to achieve this.

In some embodiments, the ultrasound imaging apparatus includes a sensor for detecting when the dual function charging and cooling unit is attached. In some embodiments, the sensor includes at least a portion of a resistor network. In some embodiments, the resistor network includes a resistor voltage divider network. In some embodiments, sensor is a magnetic sensor within a housing of the of the ultrasound imaging apparatus and most preferably such magnetic sensor is embedded in the electronic circuitry (for example, a PCB circuit). Such a magnetic sensor detects a threshold of a magnetic field, within a vicinity and reports such detection to a processor, within the ultrasound imaging apparatus.

In some embodiments, the ultrasound imaging apparatus provides power to the dual function charging and cooling unit while the active cooling element is cooling the ultrasound imaging apparatus, when the two units are coupled. In some embodiments, the ultrasound imaging apparatus and the dual function charging and cooling unit comprise, respectively, a power accepting interface and a power conveying means therebetween, when coupled. In some embodiments, a connection between the ultrasound imaging apparatus and the dual function charging and cooling unit comprises at least one of an electronic connection (such as, for example, spring-loaded pins and landing/target point mating or USB-C mating on each unit) and a wireless connection (employing, for example, induction coils and supporting electronics in both the ultrasound imaging apparatus and the dual function charging and cooling unit).

In some embodiments, the dual function charging and cooling unit is powered independently, for example by an internal battery for powering the active cooling element. In some embodiments, the battery within the dual function charging and cooling unit also powers the ultrasound imaging apparatus.

In some embodiments, the ultrasound imaging apparatus includes a shell, and wherein said shell protects from ingress into an interior of the ultrasound imaging apparatus. In some embodiments, the shell protects of the interior of the ultrasound imaging apparatus from ingress of fluids and dust. In some embodiments, the power accepting interface has no ingress points. In some embodiments, the power accepting interface is substantially integral with the shell of the ultrasound imaging apparatus to protect from the ingress of contaminants.

In another broad aspect of the present disclosure, there is provided a method of detecting presence of a compatible dual function charging and cooling unit for attaching to an ultrasound imaging apparatus, the method including: providing a sensor on one of: the ultrasound imaging apparatus, and the dual function charging and cooling unit; providing an identity interface on the other of: the ultrasound imaging apparatus, and the dual function charging and cooling unit; when the dual function charging and cooling unit is attached, the identity interface is read through the sensor; and the attached the dual function charging and cooling unit is detected to be compatible if the reading of the identity interface matches an expected reading.

In some embodiments, the method may be considered a method of determining whether a dual function charging and cooling unit is attached to an ultrasound imaging apparatus and/or whether or not it is compatible with said ultrasound imaging apparatus.

In some embodiments, the sensor is provided on the ultrasound imaging apparatus and the identity interface is provided on the dual function charging and cooling unit.

In some embodiments, the ultrasound imaging apparatus comprises a first electrical connector capable of supplying current and the dual function charging and cooling unit comprises a second electrical connector that interfaces with the first electrical connector. When the cooling unit is attached and determined to be compatible, the ultrasound imaging apparatus activates the first electrical connector to supply electric current to the second connector so that the cooling unit is powered.

In some embodiments, the dual function charging and cooling unit comprises a first electrical connector capable of supplying electric current and the ultrasound imaging apparatus comprises a second electrical connector that interfaces with the first electrical connector. When the dual function charging and cooling unit is coupled and determined to be compatible, the first electrical connector is activated to supply electric current to the second connector so that the ultrasound imaging apparatus is powered.

In some embodiments, the first electrical connector is prevented from supplying current if the dual function charging and cooling unit is determined to be not compatible. In some embodiments, the ultrasound imaging apparatus is prevented from imaging if the dual function charging and cooling unit is determined to be not compatible.

In some embodiments, the sensor is provided on the dual function charging and cooling unit and the identity interface is provided on the ultrasound imaging apparatus. In some embodiments, the dual function charging and cooling unit is prevented from activating if the dual function charging and cooling unit is determined to be not compatible with the ultrasound imaging apparatus.

In another broad aspect of the present disclosure, there is provided a dual function charging and cooling unit for an ultrasound imaging apparatus, the cooling unit comprising a housing comprising a fastener for detachably coupling the dual function charging and cooling unit to the ultrasound imaging apparatus; a power conveying element to convey power to the ultrasound imaging apparatus, when coupled; and an active cooling element enclosed in the housing and configured to remove heat from power conveying element, when coupled.

In some embodiments, the active cooling element comprises a fan configured to direct air onto or away from an external surface of the ultrasound imaging apparatus.

In some embodiments, the power conveying element comprises a power port for mating with a detachable power cord and, as such, the dual function charging and cooling unit acts a conduit for conveyance of power to the ultrasound imaging apparatus, when coupled to both the detachable power cord and the ultrasound imaging apparatus.

In some embodiments, the dual function charging and cooling unit comprises a battery for: i) powering the operation of the active cooling element; and/or ii) powering the operation of the ultrasound imaging apparatus.

In some embodiments, the dual function charging and cooling unit comprises a power conveying element which wirelessly conveys power to a power accepting interface on/within an ultrasound imaging apparatus when coupled thereto.

In other embodiments, the dual function charging and cooling unit comprises a power conveying element which is an electronic connection point, for conveying power to a matable electronic connection point on an ultrasound imaging apparatus power accepting interface, when coupled thereto.

In some embodiments, the dual function charging and cooling unit housing includes at least one air inlet and at least one air outlet. In some embodiments, a size of the air inlet is different (e.g., larger) from the size of the air outlet to induce a pressure differential.

As indicated above, two issues associated with ultra-portable ultrasound imaging devices are appropriate heat dissipation during scanning and long-term powering of such devices, particularly (although not exclusively) in reference to built-in, non-removable, rechargeable batteries contained therein. Scanning time is greatly reduced if the ultrasound imaging device must be placed in a charging dock in the midst of usage due to charge deficiencies. If, as a solution, an ultra-portable ultrasound imaging device is tethered to a power cord to convey power during operation (for example, via a USB port), there remains the issue of heat dissipation, which is increased during simultaneous scanning and charging. This additional heat generation is even more marked in compact scanners. A partial solution is provided in U.S. patent application Ser. No. 15/614,488 filed Jun. 5, 2017 and published as 2018/0344294, (the entire contents of which are incorporated herein by reference) in which a fan clip with an active cooling element (such as, for example, a fan) is removably attached to an ultrasound scanner during usage. In this solution, there is no means to "in use" power the ultrasound imaging device and the latter powers the fan clip during such coupling, thereby reducing use time and efficiency of the scanner. The dual function charging and cooling unit of the present invention provides a functional solution to both of these issues: in use (i.e. while scanning) power conveyance to charge a rechargeable battery within the ultrasound imaging device (such power conveyance in different embodiments being either tethered or cordless/wireless) while the ultrasound imaging device is coupled to dual function charging and cooling unit which additionally comprises an active cooling element to dissipate heat generated during scanning.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a schematic representation of an ultrasound imaging system, in accordance with at least one embodiment of the present invention. As shown, the ultrasound imaging system includes an ultrasound imaging apparatus 110 and a dual function charging and cooling unit 130 that can detachably couple to the ultrasound imaging apparatus 110.

The ultrasound imaging apparatus 110 may contain a transducer 114 which may be configured to emit ultrasound energy signals towards an object and receive echoes of the ultrasound energy signals that reflect off the object. Transducer 114 may be electrically connected to electronics 116 which can control the transducer 114 and process the received echoes into ultrasound image data. Ultrasound imaging apparatus 110 may have a battery 118 for providing power to the electronics 116. Preferably, it is an internal, non-removable rechargeable battery. Ultrasound imaging apparatus 110 may have a heat dissipater 120 that receives heat from the electronics 116 and/or transducer 114 and/or battery 118 during operation. Dual function charging and cooling unit 130 may include a fastener 136 for facilitating the detachable physical coupling of the dual function charging and cooling unit 130 to the ultrasound imaging apparatus 110. When it is attached, dual function charging and cooling unit 130 can be configured to remove heat from the ultrasound imaging apparatus' heat dissipater 120 using active cooling element 140. Dual function charging and cooling unit 130 may include a unit connector 132 that electrically connects to the corresponding apparatus connector 122 on the ultrasound imaging apparatus 110 when dual function charging and cooling unit 130 is coupled to ultrasound imaging apparatus 110. In various embodiments, the connection between unit connector 132 and apparatus connector 122 may serve one or more different purposes. For example and without limitation, the interface/connection between unit connector 132 and apparatus connector 122 may: i) enable ultrasound imaging apparatus 110 to provide power to active cooling element 140 within dual function charging and cooling unit 130; ii) enable ultrasound imaging apparatus 110 to determine when a compatible dual function charging and cooling unit 130 is attached; iii) enable dual function charging and cooling unit 130 to convey power, directly or indirectly, to ultrasound imaging apparatus 110; and iv) enable a variety of communications between ultrasound imaging apparatus 110 and dual function charging and cooling unit 130 in response to outputs of one or more sensors housed within ultrasound imaging apparatus 110 (for example, in response to an output of a temperature sensor within ultrasound imaging apparatus 110, causing electronics 133 to switch active cooling element 140 on and off, as required).

It is to be understood that the term connection or interface, for example, with reference to power conveying element (here, unit connector 132) and power accepting interface (here, apparatus connector 122) refers to a broad array of connectivity, signalling, power conveyance and communication options between the dual function charging and cooling unit and the ultrasound imaging apparatus. In one preferred embodiment, as shown in FIGS. 2, 4, 5 and 11 and described in further detail below, the power conveying element of the dual function charging and cooling unit may comprise one or more spring-loaded pins (also referred to as spring-loaded contacts, spring probes, or pogo pins), and the power accepting interface of the ultrasound imaging apparatus may comprise one or more respective target or landing surfaces for such spring-loaded pins. Spring-loaded pins may be easily integrated into an apparatus mating surface of the dual function charging and cooling unit, with numerous options available in terms of height, travel and spring force. Contact to a unit mating surface on the ultrasound imaging device, on which are disposed a plurality of target or landing surfaces, is made with each spring pin plunger tip. The spring pin allows for easy and convenient blind mating and some misalignment when coupling the dual function charging and cooling unit to the ultrasound imaging device.

Figure 12:
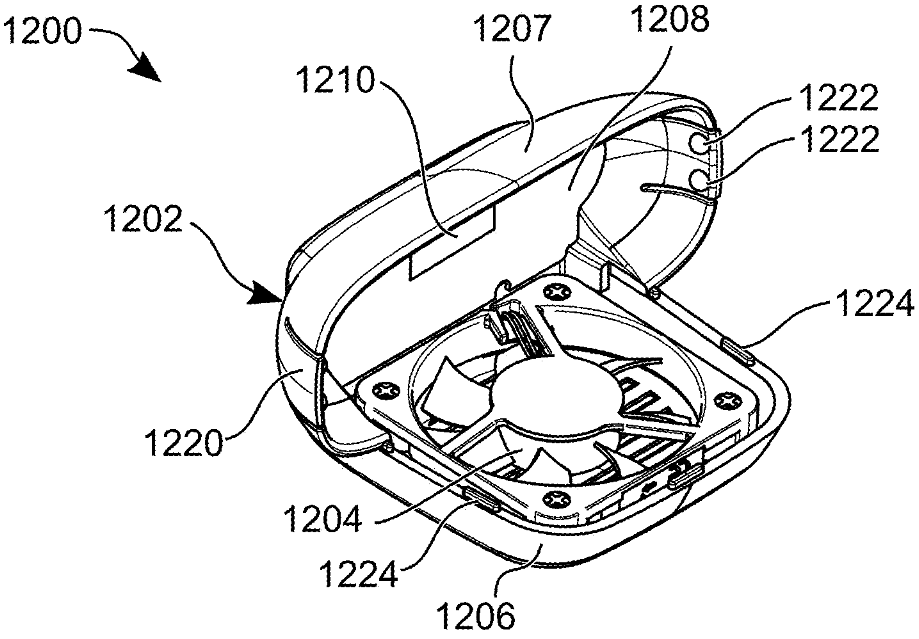
FIG. 12 shows a perspective view of a dual function charging and cooling unit, in accordance with at least one embodiment of the present invention.
Figure 13:
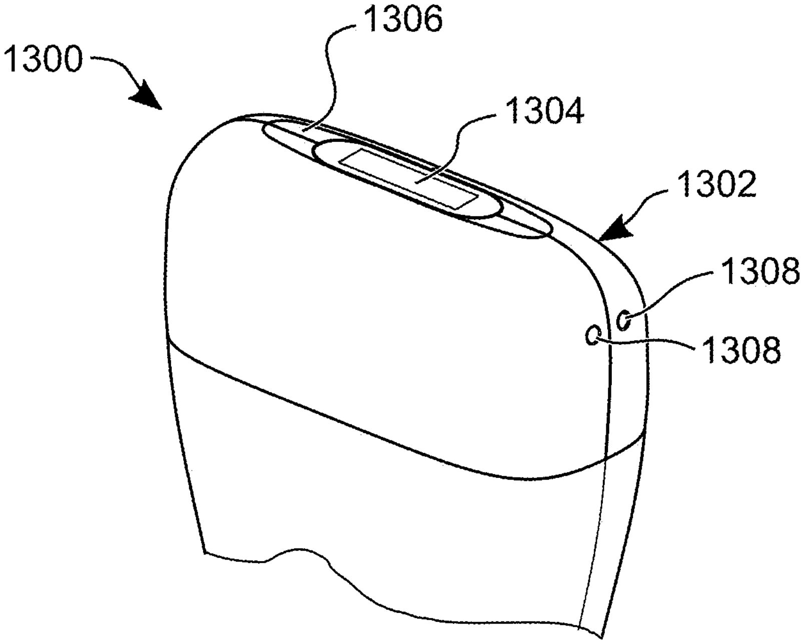
FIG. 13 shows a perspective view in partial cut-away of an end of an ultrasound imaging apparatus, of a dual function charging and cooling unit, in accordance with at least one embodiment of the present invention.

In another preferred embodiment, as shown in FIGS. 12 and 13, and described in further detail below, the power conveying element of the dual function charging and cooling unit and the power accepting interface of the ultrasound imaging apparatus may each comprise induction coils (and associated electronics) for wireless charging. It is to be understood that these are not the only modes of connection between the power conveying element of the dual function charging and cooling unit and the power accepting interface of the ultrasound imaging apparatus and are provided by way of example only.

Figure 8:
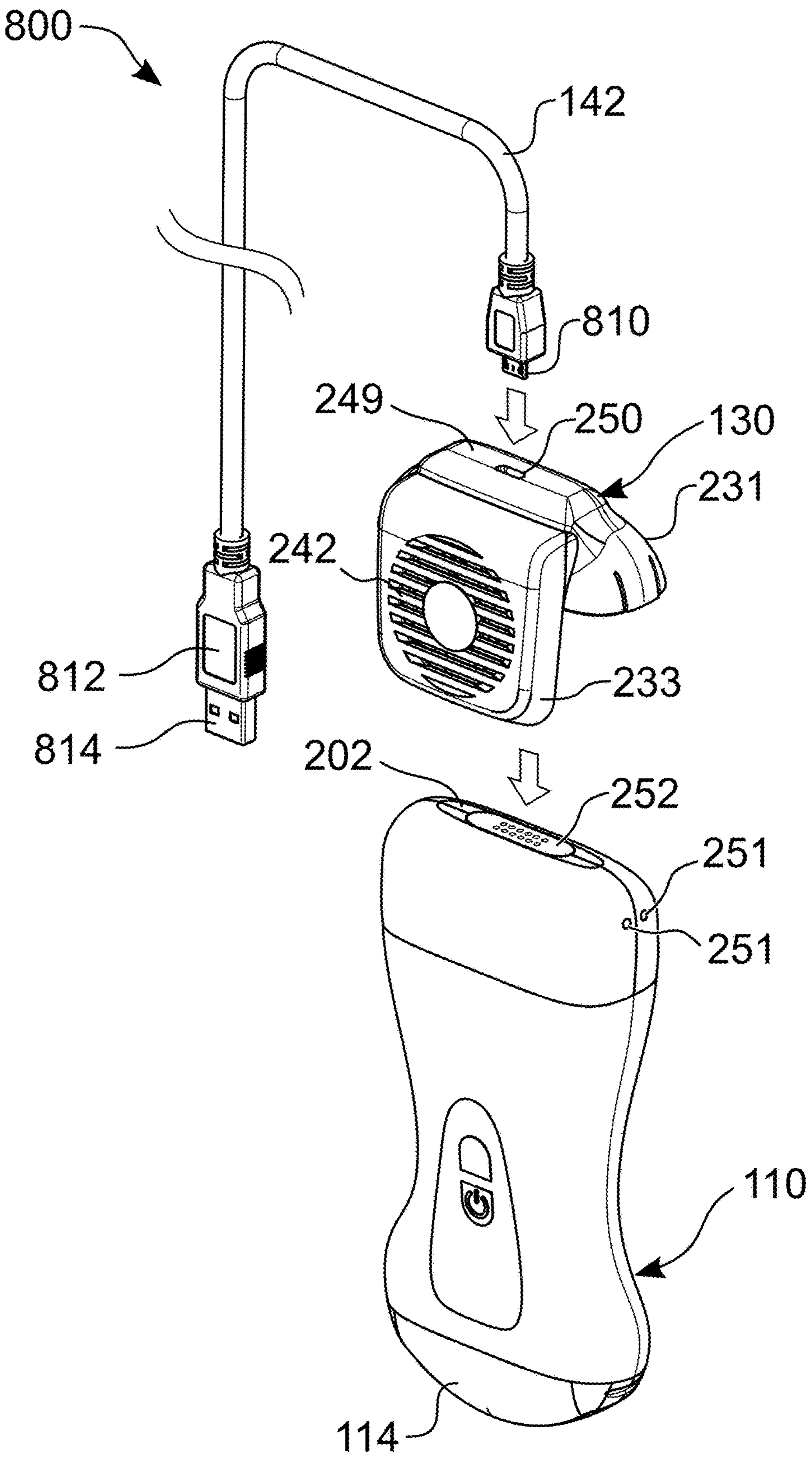
FIG. 8 shows a perspective view of an ultrasound imaging system with a dual function charging and cooling unit in a detached state and poised above for coupling to an ultrasound imaging apparatus, along with a power cord provided above the dual function charging and cooling unit, with directional arrow for attachment, in accordance with at least one embodiment of the present invention.
Figure 9:
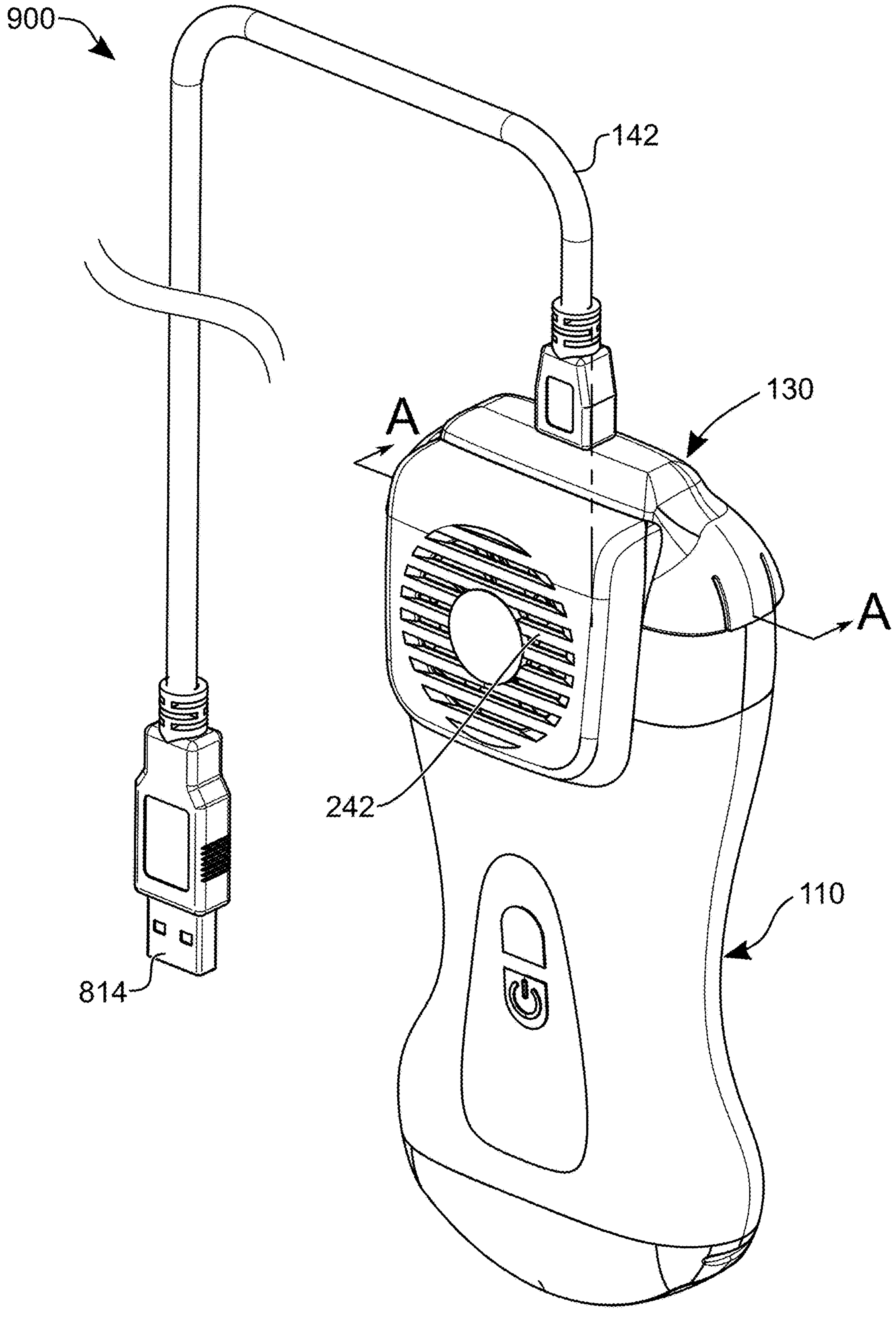
FIG. 9 shows a perspective view of the ultrasound imaging system of FIG. 8, with the dual function charging and cooling unit coupled to the ultrasound imaging apparatus, and the power cord attached to the dual function charging and cooling unit, in accordance with at least one embodiment of the present invention.

In some embodiments, the power conveying element of the dual function charging and cooling unit 130 may convey power, directly or indirectly to the power accepting interface of the ultrasound imaging apparatus 110. For example, as shown in FIGS. 8 and 9, and described in further detail below, indirect conveyance of power may include the power conveying element of the dual function charging and cooling unit 130 comprising a power port for mating with a detachable power cord, and an electronic assembly to power the ultrasound imaging apparatus, and wherein the power accepting interface of the ultrasound imaging apparatus 110 accepts said power from the detachable power cord and electronic assembly, when the ultrasound imaging apparatus is coupled to the dual function charging and cooling unit. In this way, the dual function charging and cooling unit 130 simply acts as a conduit to enable a tethered or corded power source to convey power to the ultrasound imaging apparatus. Such a tethered power connection enables battery 118 within ultrasound imaging apparatus 110 to be charged during scanning. In some embodiments, while such a tethered power connection powers battery 118, the active cooling element 140 of the dual function charging and cooling unit 130 operates to dissipate heat on heat dissipator 120. In some embodiments, battery 118 additionally conveys power to operate the active cooling element 140 of the dual function charging and cooling unit 130 via a current connection means between the ultrasound imaging apparatus 110 and the dual function charging and cooling unit 130. Such a current connection means may comprise the mating spring-loaded pins and target or landing surfaces or a wireless connection through induction coils.

Figure 10:
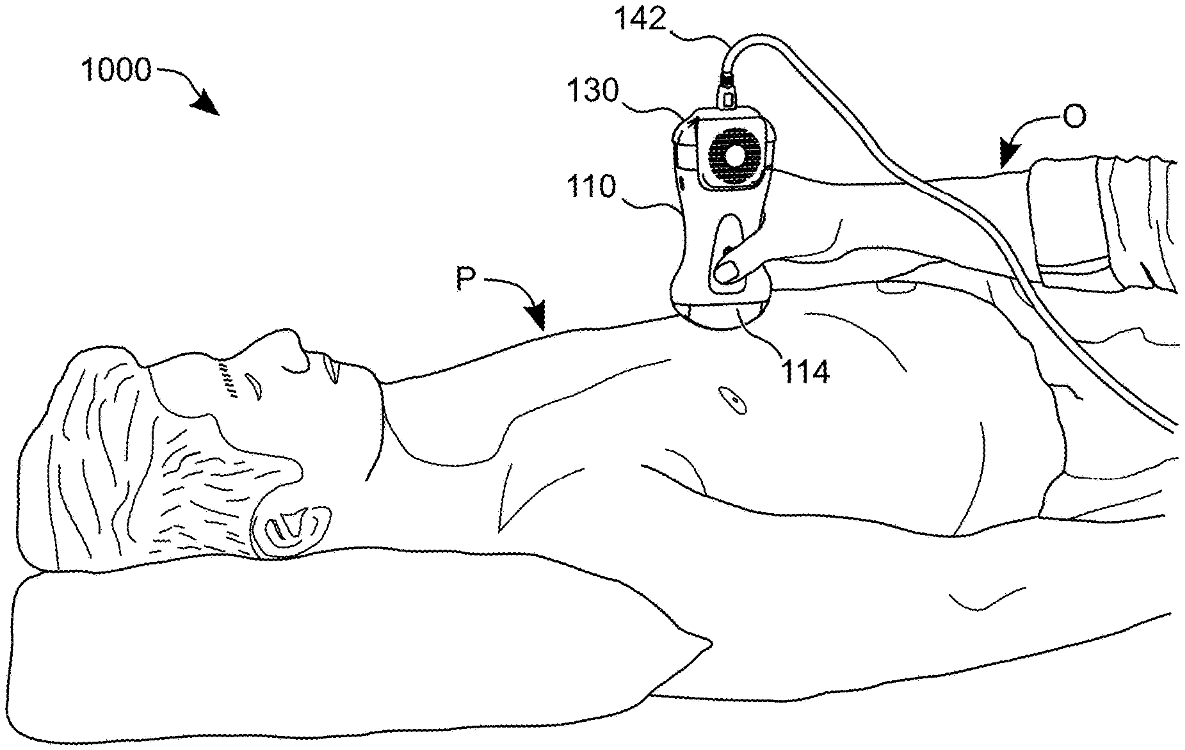
FIG. 10 shows a side view of the ultrasound imaging system of FIG. 9, with the dual function charging and cooling unit coupled to the ultrasound imaging apparatus, the power cord attached to the dual function charging and cooling unit, and the power cord plugged into a power source and an operator scanning a patient using the ultrasound imaging apparatus, in accordance with at least one embodiment of the present invention.

Referring back to FIG. 1, there is provided a power source connector 134 for the dual function charging and cooling unit 130 to receive an external power source 138 shown in dotted outline and to convey power therefrom to ultrasound imaging apparatus 110. Such an external power source 138 may be conveyed by a power cord 142 (as shown for example in FIG. 8) and is shown in dotted outline as an optional or removable component within system 100. Power Source connector 134 (schematically shown in FIGS. 2 and 3 as 250) may comprise a power port and may be selected from the group consisting of a micro B Universal Serial Bus (USB), a micro B USB, a micro USB 3 and a USB C. Connector 134 communicates with electronics 133, within the dual function charging and cooling unit 130 which in turn communicates with connector 132 and active cooling element 140. Power cord 142 may be attached to connector 134 and dual function charging and cooling unit 130 may be coupled to ultrasound imaging apparatus 110 during operation of ultrasound imaging apparatus 110, as shown in FIG. 10 thereby conveying power to battery 118 in ultrasound imaging apparatus 110 (via connector 134, electronics 133, connector 132, connector 122, electronics 116 and battery 118). In some embodiments, upon coupling of ultrasound imaging apparatus 110 and dual function charging and cooling unit 130, active cooling element 140 may be powered by battery 118 via electronics 133, connector 122, connector 132, and electronics 133.

In some embodiments, electronics 133 includes a microcontroller which controls the operation of the active cooling element according to commands transmitted by ultrasound imaging apparatus 110 via connector 122 to connector 132 within dual function charging and cooling unit 130. In some embodiments, the ultrasound imaging apparatus is wirelessly connected to a user interface device which transmits control signals to the ultrasound imaging apparatus (electronics 116) and to the dual function charging and cooling unit 130 (electronics 133). In other embodiments, the dual function charging and cooling unit 130 is activated by an activation means (for example a push button located on the unit) or is activated by a user interface device communicably coupled to the ultrasound imaging apparatus 110 and/or dual function charging and cooling unit 130.

In some embodiments, the connection between ultrasound imaging apparatus 110 and dual function charging and cooling unit 130 is through a wireless, radio-wave based, communication interface such as a Bluetooth interface.

During operation, ultrasound imaging apparatus 110 may transmit ultrasound image or other data to a tertiary device for display or storage. For example, ultrasound imaging apparatus 110 may transmit data via a wired or wireless connection to a multi-use electronic display device to display an ultrasound image.

While various embodiments of the invention describe removably corded conveyance of recharging power to battery 118 of ultrasound imaging apparatus 110, employing the dual function charging and cooling unit 130 as a power conduit, it is preferred, in other embodiments to convey such battery charging power via a separate internal battery within the dual function charging and cooling unit 130 (shown within casing 816 in FIG. 8), thus enabling a fully cordless operation of the system. Such separate internal battery within the dual function charging and cooling unit 130 may be rechargeable via a power cord as described herein or via wireless charging through a charging dock, surface or platform.

Figure 2:
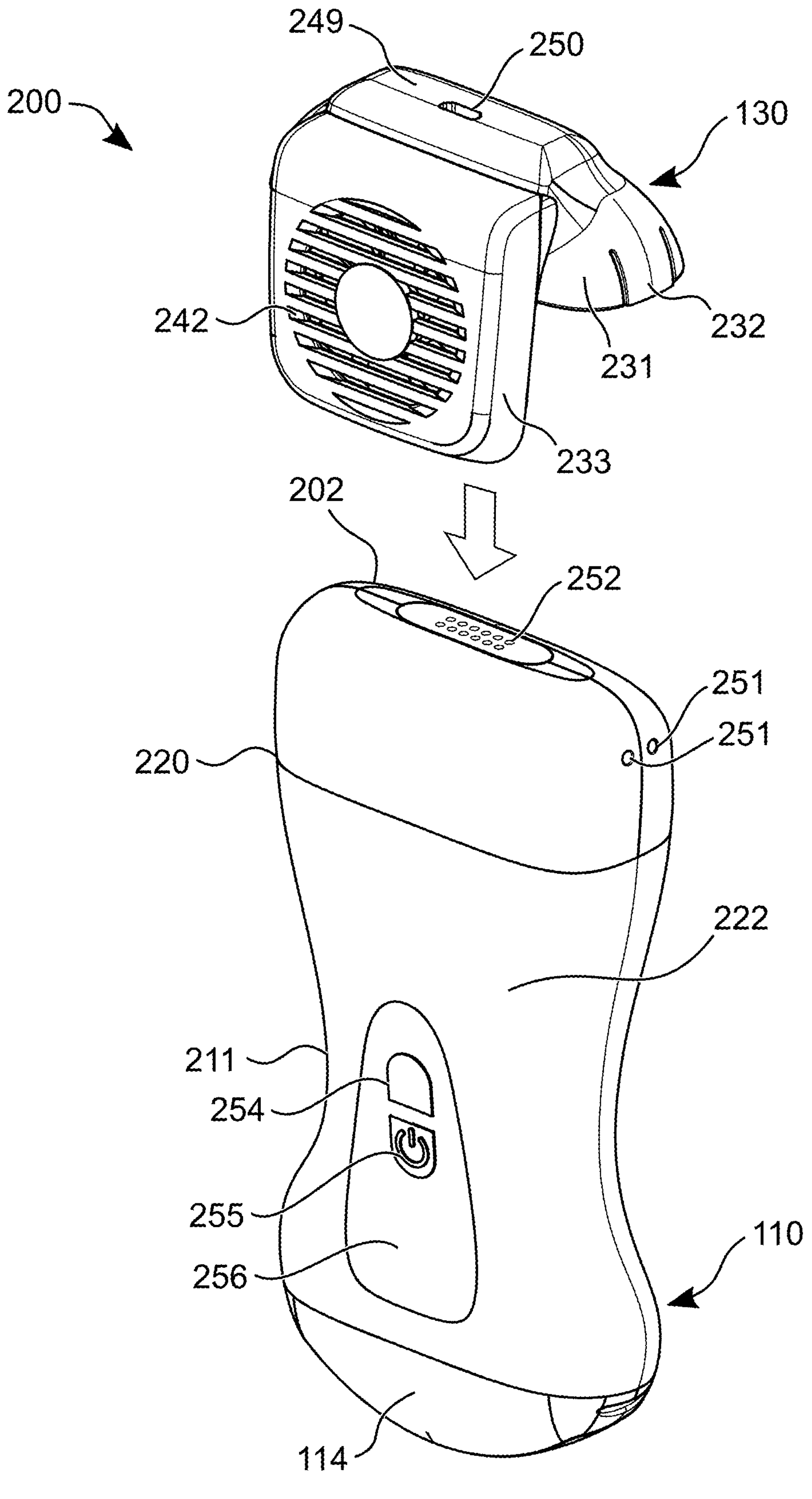
FIG. 2 shows a perspective view of an ultrasound imaging system with a dual function charging and cooling unit in a detached state and poised above for coupling to an ultrasound imaging apparatus, in accordance with at least one embodiment of the present invention.
Figure 3:
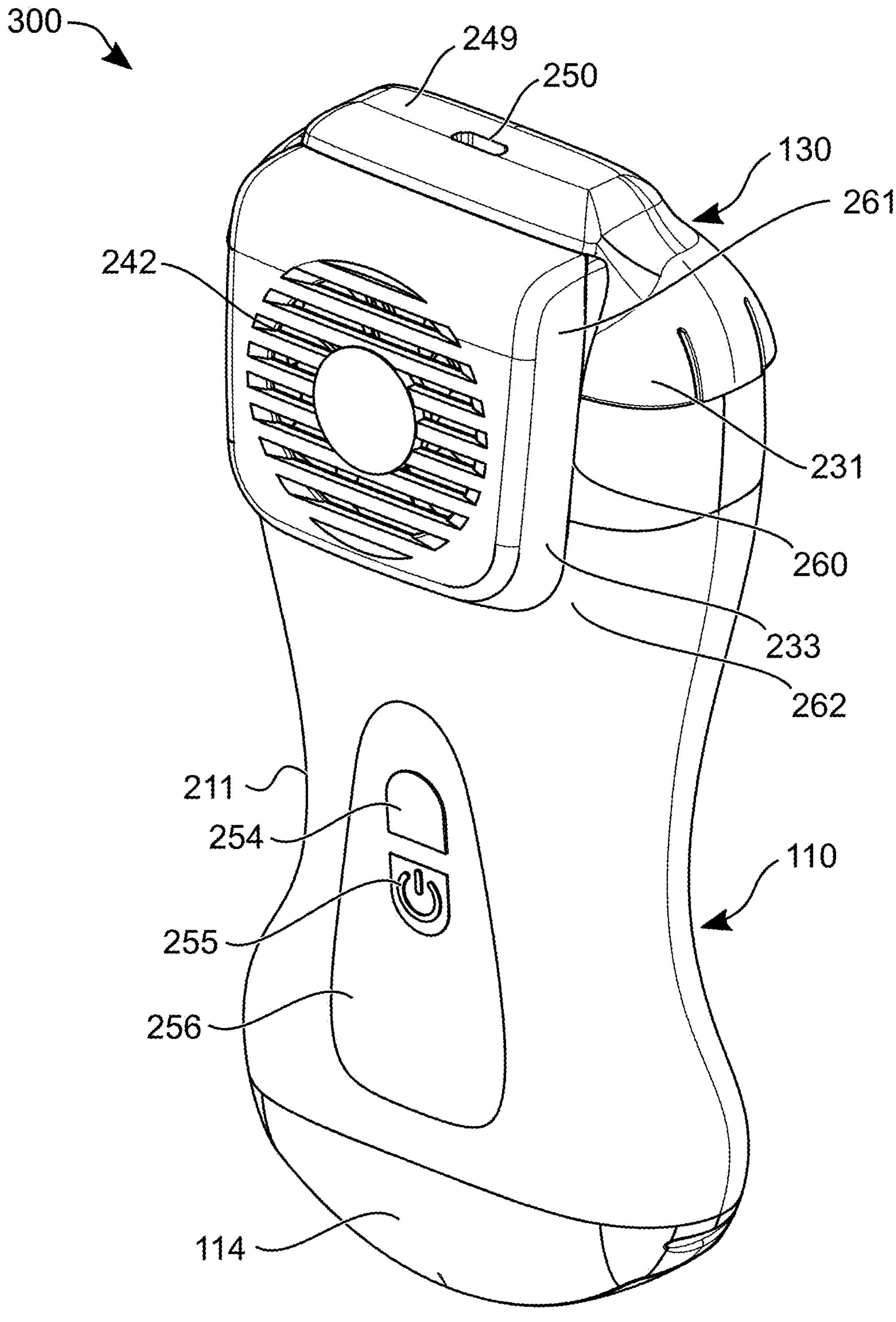
FIG. 3 shows a perspective view of an ultrasound imaging system with a dual function charging and cooling unit in an attached (coupled) state to an ultrasound imaging apparatus, in accordance with at least one embodiment of the present invention.

Referring to FIG. 2 and FIG. 3 shown there generally as 200 is a perspective view of an example embodiment of an ultrasound imaging system, in accordance with at least one example embodiment of the present invention. FIG. 2 shows ultrasound imaging system 200 with ultrasound imaging apparatus 110 and dual function charging and cooling unit 130 in a detached state but with an arrow disposed to show a connection direction (dual function charging and active cooling unit 130 capping down over top end 202 of ultrasound imaging apparatus 110. FIG. 3 shows the same ultrasound imaging system, noted as 300, with ultrasound imaging apparatus 110 and dual function charging and cooling unit 130 in an attached or coupled state.

With reference to both FIG. 2 and FIG. 3, the ultrasound imaging apparatus 110 generally has a shell 211 which may be connected to a transducer array 114 and, internal to the shell, the processing components. As the ultrasound imaging apparatus 110 is used to perform imaging, heat may be generated by the transducer array 114 and/or the processing components (e.g., the electronics 116 shown in FIG. 1) and/or the battery 118. As shown in FIG. 2, a heat dissipater 120 shown in FIG. 1 is provided as side surface 220 on the shell 211 of the ultrasound imaging apparatus 110. Alternatively, the heat dissipater 120 may be provided in the form of fins extending across body 222 of the shell 211 to help to passively dissipate heat from the ultrasound imaging apparatus 110 using natural convection. While fins may generally provide a sufficient level of heat dissipation, it may be desirable to further enhance the heat dissipation in certain circumstances. For example, further enhancing the heat dissipation may allow for continuous scanning by the ultrasound imaging apparatus 110 over a lengthy period. Various heat dissipation configurations are known in the art.

To increase the heat dissipated from ultrasound imaging apparatus 110, dual function charging and cooling unit 130 may be attached (as shown in FIG. 3). Dual function charging and cooling unit 130 generally has a cap portion 231 and may also include a fastener arrangement for detachably coupling the dual function charging and cooling unit 130 to the ultrasound imaging apparatus 110. In the example embodiment of FIGS. 2 and 3, the fastener arrangement is formed with the cap portion 231 as a cap grip portion 232 that facilitates attachment of the dual function charging and cooling unit 130 to the ultrasound imaging apparatus 110. In one embodiment, cap grip portion 232 (shown as 1220 in FIG. 12) comprises a plurality of nubs or protrusions (shown best as 1222 in FIG. 12, and as 401 in FIG. 4) is with two nubs on each cap grip portion) which each nest or snap within respective apertures (shown as 1308 in FIG. 13, 251 in FIGS. 2 and 510 in FIG. 5) when the dual function charging and cooling unit is coupled to the ultrasound imaging apparatus. The cap portion 231 may also include air inlets 242 (422 in FIG. 4) for air ingress (directly shown as arrow 424 in FIG. 4). In some embodiments, air egress is via purpose-created gaps in the coupling of the dual function charging and cooling unit to the ultrasound imaging apparatus to allow air to flow past and/or through the active cooling element. This is shown best in FIG. 3, at point 260, which represents a space or gap between cooling unit wall 261 and shell surface 262. Also, attention is drawn to FIG. 4 which illustrates spacers 426 (here, raised blocks disposed on upper ledge of active cooling element housing 233). Spacers 426 create a space or channel between the dual function charging and cooling unit (around at least part of the active cooling element) and the shell of the ultrasound imaging apparatus for air egress. Alternatively, vents or apertures may be built into the dual function charging and cooling unit for air egress.

In this illustrated embodiment, the dual function charging and cooling unit 130 attaches to ultrasound imaging apparatus 110 using a fastener provided in the form of a cap grip portion 232. Cap grip portion 232 can be formed integrally with cap portion 231 but provided with flexible cut-aways to allow the cap grip portion 232 to flex around/over the shell 211 and snap on/off of the ultrasound apparatus 110. In imaging various embodiments, the material of cap grip portion 232 and/or the cap portion 231 of the dual function charging and cooling unit 130 may be selected to provide additional heat conduction from shell 211 to active cooling unit 140. Alternatively, the dual function charging and cooling unit 130 attaches to ultrasound imaging apparatus 110 using magnetic fasteners as shown in FIG. 1 (as 136) and in FIG. 6. The coupling mechanism (whether magnetic or otherwise) may be releasable without the use of tools. However, in some embodiments, the use of tools for releasing the dual function charging and cooling unit 130 may be possible or desired.

Further in this illustrated embodiment, dual function charging and cooling unit 130 additionally comprises active cooling element housing 233 (comprising active cooling element 140) extending downwardly from the cap portion 231 such that when the dual function charging and cooling unit 130 (specifically, cap portion 231) is coupled over top end 202 of ultrasound imaging apparatus 110, the active cooling element housing 233 secures and holds active cooling element 140 directly over side surface 220 (heat dissipator) of the ultrasound imaging apparatus. This close and secure positioning facilitates optimal heat transfer. Active cooling element housing 233 and cap portion 231 may be fully integral or formed of conjoined pieces. In a preferred embodiment the shell is comprises of metal alloy, to increase the efficiency of heat dissipation.

Still referring to FIG. 2 and FIG. 3, the dual function charging and cooling unit 130 additionally comprises a power conveying element or power connector in the form of a USB A port 250 disposed through top surface 249 of cap portion 231 of dual function charging and cooling unit 130. Current for recharging battery 118 passes through connector 132, connector 122 to charger and battery 118 as best seen schematically in FIG. 6. Top end 202 of ultrasound imaging apparatus 110 additionally comprises a power accepting interface, here in the form of a plurality of (two rows of six) landing or target points 252. Ultrasound imaging apparatus 110 additionally comprises on/off control switches 254/255 on pad 256.

Figure 4:
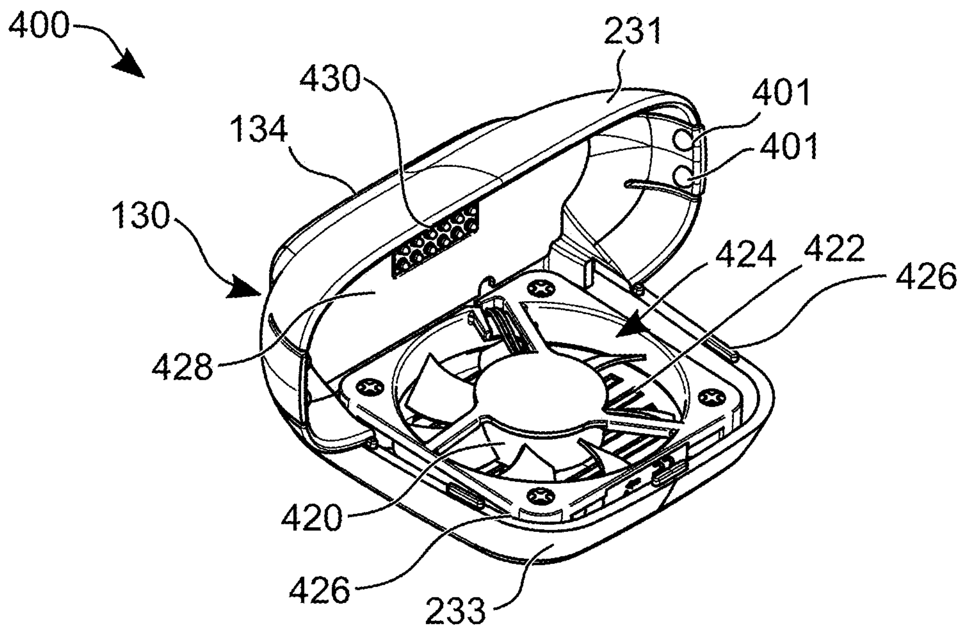
FIG. 4 shows a perspective view of a dual function charging and cooling unit, in accordance with at least one embodiment of the present invention.
Figure 5:
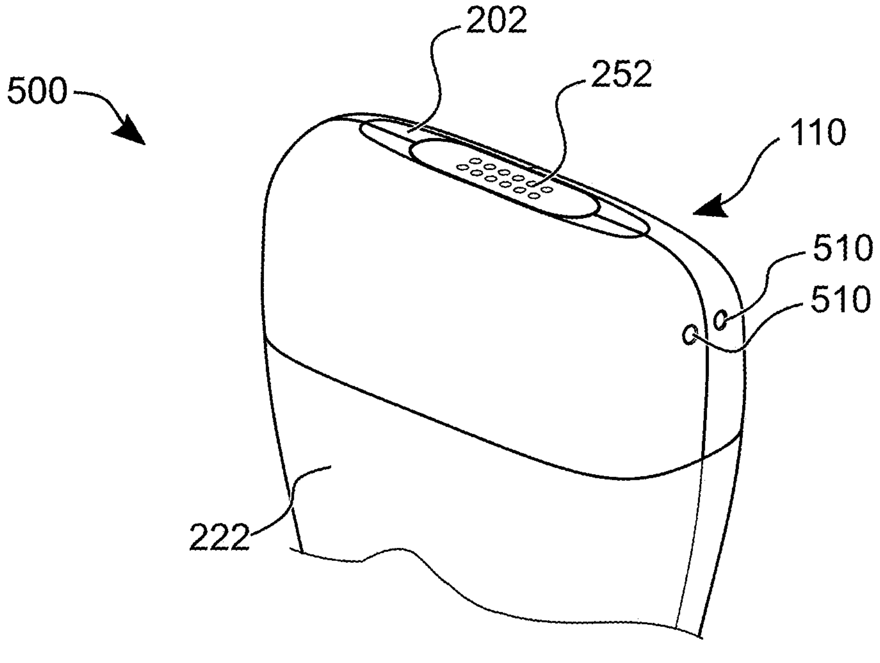
FIG. 5 shows a perspective view in partial cut-away of an end of an ultrasound imaging apparatus, of a dual function charging and cooling unit, in accordance with at least one embodiment of the present invention.

Referring to FIG. 4, shown there generally as 400 is a dual function charging and cooling unit 130 in a rear perspective view, in accordance with at least one embodiment of the present invention. As noted with respect to FIG. 1, the dual function charging and cooling unit 130 may include an active cooling element 140. In the example embodiment shown in FIG. 4, the active cooling element 140 (FIG. 1) is provided in the form of a fan 420 mounted to the active cooling element housing 233. During operation, cool air can be drawn into the dual function charging and cooling unit 130 through air inlets 422 along air inlet path 424 by fan 420. Once through fan 420, air can be directed into and along the surface 220 of the ultrasound imaging apparatus 110. Heat can then be transferred from the surface 220 to the cool air through convection. The warm air may then continue to travel along air outlet path 430 created by spacer(s) 426 in active cooling element housing 233 and into the surrounding environment. In some preferred embodiments, the cool air can be directed onto fins or ridges on the surface of the heat dissipater 120 to generate more turbulence and enhance heat transfer. It can be appreciated that those skilled in the art may choose to use a different air pathway. For example, the fan may be configured to operate so that airflow is in the reverse direction so as to draw air away from an external surface of the ultrasound imaging apparatus 110.

Connector 134 may be mounted to cap portion 231 of the dual function charging and cooling unit 130 and may form an electrical connection to the fan 420 via electronics 133 (shown in FIG. 1). On inner surface 428 of cap portion 231, there is provided a plurality of spring-loaded pins 430 protruding therefrom and which are arranged to connect with the landing/target points 252 on the top end 202 of ultrasound imaging apparatus 110, when the dual function charging and cooling unit 130 is coupled to thereto. More specifically, inner surface 428 of cap portion 231 aligns with top end 202 of ultrasound imaging apparatus 110 causing the connection of the spring-loaded pins and respective landing/target points. Top end 202 of ultrasound imaging apparatus 110 showing landing/target points 252 are illustrated at 500 in FIG. 5.

In some embodiments, the size and shape of air inlets 422 and spacers 426 can be configured so that the air inlets 422 are different from the air outlets created by spacers 426 (e.g., as shown, the air inlets 422 are larger). Such a configuration may create a pressure differential across the fan 420, so as to increase the pressure (and thus velocity) of the airflow downstream from the fan 420 directed at the surface 220. This, in turn, may improve heat dissipation performance. In various embodiments, the location of air inlets 422 and spacers 426 may be chosen to direct the warm air away from the operator of the ultrasound imaging apparatus 110 and/or away from the patient during scanning.

Figure 6:
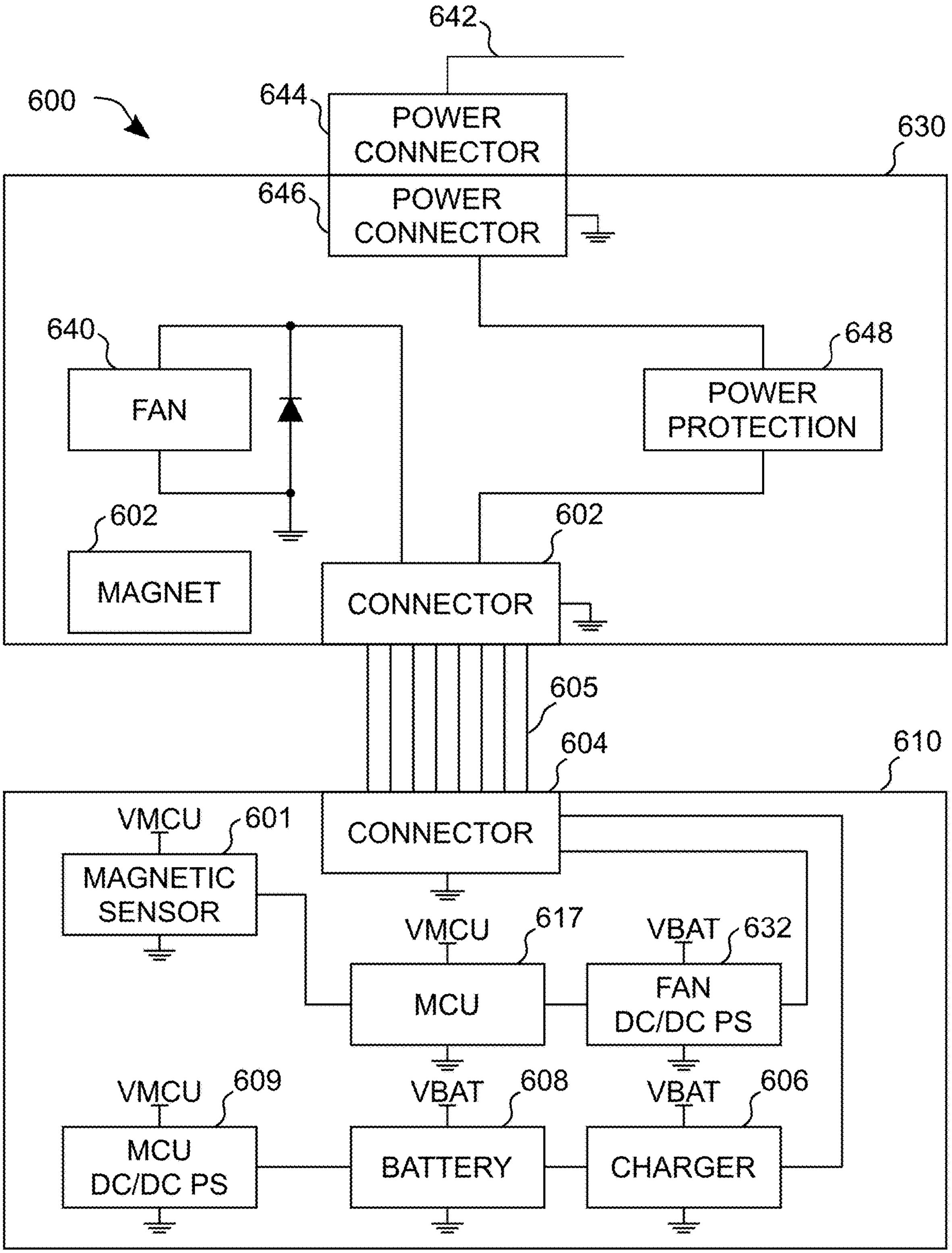
FIG. 6 shows an electrical schematic of some of the components of the ultrasound imaging system of FIGS. 1-3, in accordance with at least one embodiment of the present invention.

Referring to FIG. 6, shown there generally as 600 is an electrical schematic for dual function charging and cooling unit 130 of the ultrasound imaging system 110 of FIGS. 2-3. The electrical schematic includes an ultrasound imaging apparatus portion 610 and a dual function charging and cooling unit portion 630. The apparatus portion 610 and the dual function charging and cooling unit portion 630 can be coupled via a wireless or contact connection (605) of unit connector 602 on the dual function charging and cooling unit and connector 604 on the ultrasound imaging apparatus. For example, unit connector 602 may comprise a plurality of spring-loaded pins (Ex: POGO pins) and apparatus connector 604 may comprise a plurality of landing or target points matched to the spring-loaded pins. As described herein, this is simply one exemplary mode of connection or power conveyance between the dual function charging and cooling unit and the ultrasound imaging apparatus. Apparatus connector 604 may be connected to a charger 606, which in turn is connected to internal rechargeable battery 608 which in turn is connected to processor 609 (e.g., microcontroller unit (MCU DC/DC PS)).

As dual function charging and cooling unit 130 is placed into proximity with the ultrasound imaging system 110, magnetic sensor 601 detects a magnetic field generated by magnet 602 and microcontroller/processor 604 (MCU) determines if threshold of a pre-determined magnetic field is met. Such condition being met, microcontroller/processor 604 triggers fan DC/DC 632 which is the power supply block for fan 640, power being transferred via apparatus connector 604 to unit connector 602.

The additional functionality of the system of the invention, powering the ultrasound imaging system, is illustrated here as corded connection comprising power cord 642 and micro-USB 644 although this may be achieved via any external power supply, whether via AC/DC adapter or other external means or it may be achieved by a battery within the dual function charging and cooling unit. In the embodiment illustrated in FIG. 6, when the dual function charging and cooling unit is attached to the ultrasound imaging system, micro-USB 644 engages with power connector 646. Power protection/connection block 648 monitors power status including voltage issues for example, whether there is over-voltage and whether the power being passed through the power connector is safe for the circuitry and components of the ultrasound scanner. Power passes through unit connector 602 to apparatus connector 604 to charging circuitry block/charger 606 which then charges battery 608. While battery 608 provides voltage to every block in scanner, MCU DC/DC power supply 609 is a voltage converter block converting battery voltage to a particular voltage required at each block/component within the scanner and also fan 640. For example, battery 608 depending on the charge level will require a different voltage, which is controlled by MCU DC/DC PS 609. For example, a voltage to MCU 604 of 3.3V is controlled and managed by MCU DC/DC PS 609.

Further, as discussed herein, when the dual function charging and cooling unit portion 630 is attached to the ultrasound imaging apparatus portion, processor 604 may control the flow of electricity to the fan 640 (for example, based on temperature of scanner, need for cooling, amount of charge in battery 608 etc. . . . ) and/or detect whether a dual function charging and cooling unit 630 encompassing the attached fan portion circuit is compatible.

Figure 7:
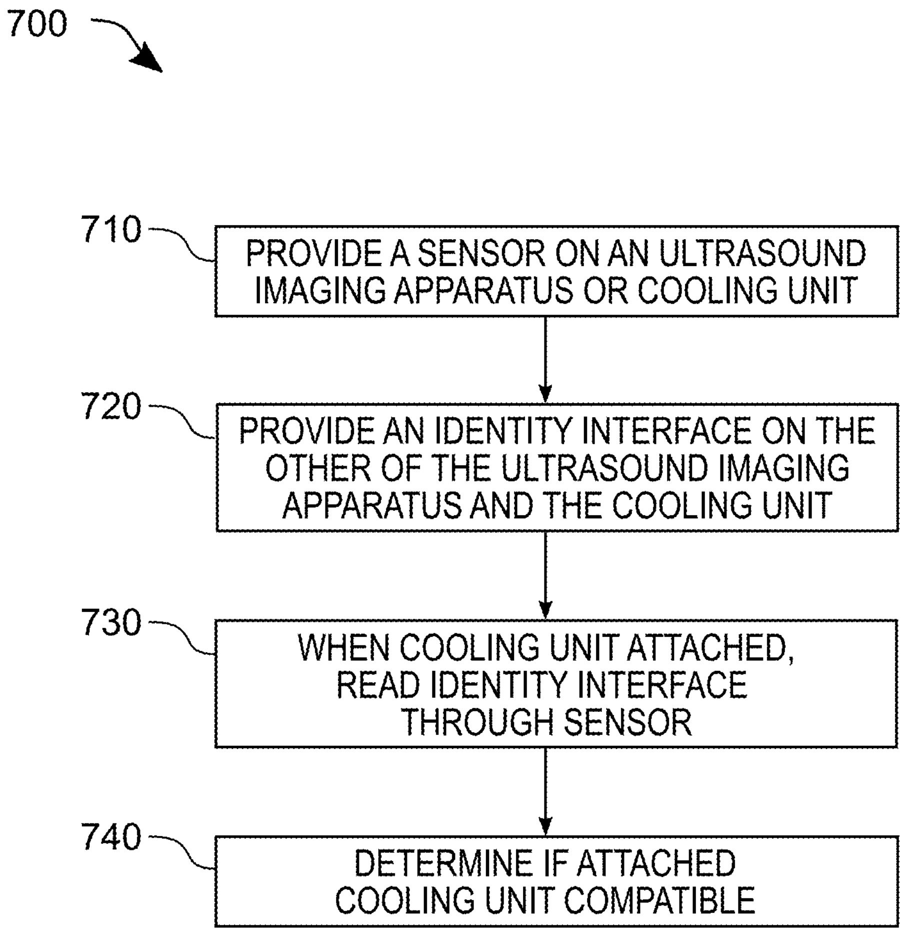
FIG. 7 is a flowchart diagram showing steps of a method for determining whether an active cooling unit is attached to and compatible with an ultrasound imaging apparatus, in accordance with at least one embodiment of the present invention.

Referring to FIG. 7, shown there generally as 700 is a flow chart depicting a method for determining whether an attached dual function charging and cooling unit is compatible with an ultrasound imaging apparatus, according to at least one embodiment of the present invention. The method may be performed by the ultrasound imaging apparatus 110. Alternatively, the method may be performed by the cooling unit 130.

At 710, a sensor may be provided on an ultrasound imaging apparatus 110 or a dual function charging and cooling unit 130. The sensor may be any suitable component or combination of components that allows for reading an identity interface. For example, as noted, the portion of the detection circuit like that which is provided on the apparatus portion 601 (e.g., including a portion of a voltage divider circuit and processor 604) may be considered a sensor.

At 720, an identity interface may be provided on the other of the dual function charging and cooling unit 130 and the ultrasound imaging apparatus 110. The identity interface may be any component (or combination of components) that allows a corresponding sensor to determine whether a dual function charging and cooling unit 130 is compatible. For example, in the detection circuitry of FIG. 6, the identity interface may include a resistor with a predetermined resistance that completes the voltage divider circuit in the sensor when the dual function charging and cooling unit 130 having the cooling unit portion 640 is attached to the ultrasound apparatus 610.

At 730, the sensor may read the identity interface when the dual function charging and cooling unit 130 is attached to the ultrasound imaging apparatus 110. The reading of the identity interface may be performed in various ways. For example, in the example embodiment of FIG. 6 where the sensor 601 is a portion of a voltage divider circuit, the reading may be performed by a processor 604 taking periodic voltage measurements as discussed above. When the dual function charging and cooling unit 130 is attached, a voltage can be read and compared with a predetermined value.

At 740, the compatibility of the dual function charging and cooling unit 130 is determined. Compatibility may be determined in various ways. For example, determining compatibility may involve comparing a value read at act 730 with one or more predetermined values. As discussed above, in example embodiment where the identity interface includes a resistor, these predetermined values may be an expected range of resistance values for resistors that have been selected for inclusion in compatible dual function charging and cooling unit 130. In the manner discussed, the identity interface may serve to "identify" the dual function charging and cooling unit 130 to the imaging apparatus 110. This may help ensure any attached dual function charging and cooling unit 130 used with the imaging apparatus 110 is not counterfeit and/or has met sufficient quality and safety standards.

If the dual function charging and cooling unit 130 is determined to be incompatible, one or more different actions may be taken. For example, the operator may be alerted. Additionally, or alternatively, if the dual function charging and cooling unit 130 would normally receive power from the ultrasound imaging apparatus 110 through an electrical connection, the power may be disabled. Additionally, or alternatively, the ultrasound imaging apparatus 110 may be prevented from imaging.

If the dual function charging and cooling unit is determined to be compatible, one or more other actions may be taken. For example, as noted, the ultrasound imaging apparatus 110 may provide electrical power through an electrical connection to power and activate the dual function charging and cooling unit 130. If the active cooling unit 130 is independently powered, the ultrasound imaging apparatus may instruct the active cooling unit 130 to begin cooling. Further, the dual function charging and cooling unit 130 may convey power to the ultrasound imaging apparatus, directly or indirectly, including through a wireless connection or via an electronic connection such as for example via the mating of spring-loaded pins and respective target points.

While the illustrated embodiment provides an identity interface in the form of a resistor being part of a voltage divider circuit (with the corresponding sensor being the remaining portion of the voltage divider circuit), different embodiments may provide an identity interface and corresponding sensor in various ways. For example, any combination of electrical, mechanical, digital, optical, wireless, or software-based components can be provided as an identity interface, and a suitable sensor may be used for identifying the identity interface and determining compatibility. Also, as illustrated herein, the sensor is provided on the ultrasound imaging apparatus 110 and the identity interface is provided on the dual function charging and cooling unit 130. However, in various embodiments, the positioning of these elements may be reversed: e.g., the sensor may be provided on the dual function charging and cooling unit 130, and the identity interface may be provided on the imaging apparatus 110.

It is also contemplated within the scope of the invention that the connection and identity interface between the dual function charging and cooling unit 130 and the ultrasound imaging apparatus 110 may be provided by magnetic fasteners/sensors. More specifically, dual function charging and cooling unit 130 may have a housing configured with at least one magnet. The at least one magnet may couple to shell 211, and thereby allow fastening of the detachable dual function charging and cooling unit 130 to the ultrasound imaging apparatus 110. In various embodiments, different arrangements of magnets could be used. For example, permanent magnets could be attached onto both the housing of the dual function charging and cooling unit and ultrasound imaging apparatus shell 211. Alternatively, permanent magnets could be attached to one of the dual function charging and cooling unit 130 or the ultrasound imaging apparatus 110; with the other component being formed with a magnetically responsive material, so as to allow a magnetic connection to be formed therebetween (e.g., mating between the dual function charging and cooling unit 130 and the ultrasound imaging apparatus 110). In some embodiments, the orientation of the magnets coupled with different polarities provide the ability to align the dual function charging and cooling unit 130 to the ultrasound imaging apparatus 110.

Although the cooling units discussed herein have generally referred to active cooling units, the methods of FIG. 7 may also be performed on passive cooling units in various embodiments. A passive cooling unit may dissipate heat without the need for electrical energy. For example, dual function charging and cooling unit 130 may include a heat sink thermally connected to a heat transfer surface. The heat transfer surface may be configured to thermally mate with the heat dissipator 120 of the imaging apparatus 110, so that heat from the imaging apparatus 110 is transferred to the heat sink and dissipated. In another example, dual function charging and cooling unit 130 may include a heat storage device to temporarily store heat from the imaging apparatus 110. As discussed herein, detecting the compatibility of a passive cooling unit may allow the ultrasound imaging apparatus to modify its operation (e.g., allow/disallow imaging, and/or modifying imaging parameters).

Referring to FIGS. 8-10, there is shown an example of coupling of the dual function charging and cooling unit 130 to the ultrasound imaging apparatus 110 and in situ (while scanning) charging of battery 118 within ultrasound imaging apparatus 110 by power cord 142, plugged in, via USB C/USB mini or micro male end 810, to USB mini or micro female port 250 on top surface 249 of the dual function charging and cooling unit 130, which serves as an intermediary or conduit to supply power from the power cord 142, in accordance with one embodiment of the invention. Power cord 142, at power source end 812 comprises a USB, USB mini or USB micro male/USB C end 814 for connection to a female port on a dock, power bank, adapter etc. . . . for the acquisition of DC power. FIG. 8 is an exploded perspective view, at 800, of each of the aforementioned three system components, in unattached form. FIG. 9 is a perspective view, at 900, of each of the aforementioned three system components, in attached/coupled form, wherein, in one aspect of the present invention: i) power is conveyed from DC power-connected power cord 142 (USB cable carrying DC power) to dual function charging and cooling unit 130 (via USB mini or micro male end 810, to USB minor micro female port 250 on top surface 249 of the dual function charging and cooling unit 130); ii) power is conveyed from dual function charging and cooling unit 130 to ultrasound imaging apparatus 110 via electronic connection points: spring-loaded pins 430 on inner surface 428 of cap portion 231 on dual function charging and cooling unit 130 to target points 252 on ultrasound imaging apparatus 110; and iii) power is conveyed from battery 118 to operate the active cooling element 140 (for example fan 242) also via electronic connection points: spring-loaded pins 430 on inner surface 428 of cap portion 231 on dual function charging and cooling unit 130 and target points 252 on ultrasound imaging apparatus 110.

FIG. 10, shows generally at 1000 a perspective view of the ultrasound system as referred to in FIG. 9, in operation. In this case, operator O is performing an ultrasound scan on patient P using ultrasound imaging device 110 (having a transducer 114), coupled to dual function charging and cooling unit 130 which is connected to a USB power cord 142. In this way, and using the system of the invention, the operator will be able to scan patient P and subsequent patients for longer periods of time, using a lightweight, compact portable ultrasound transducer, without the need for placing the unit in a dock for battery recharging. Further, the operator will be able to charge the internal battery within the lightweight, compact portable ultrasound transducer 110 indirectly via the connection to the dual function charging and cooling unit 130. At the same time, the coupled dual function charging and cooling unit 130 cools the ultrasound transducer during operation and charging, both of which generate heat within the unit. In some embodiments of the invention, the active cooling element in the dual function charging and cooling unit 130 is powered by the internal battery within the lightweight, compact portable ultrasound transducer 110.

Figure 11:
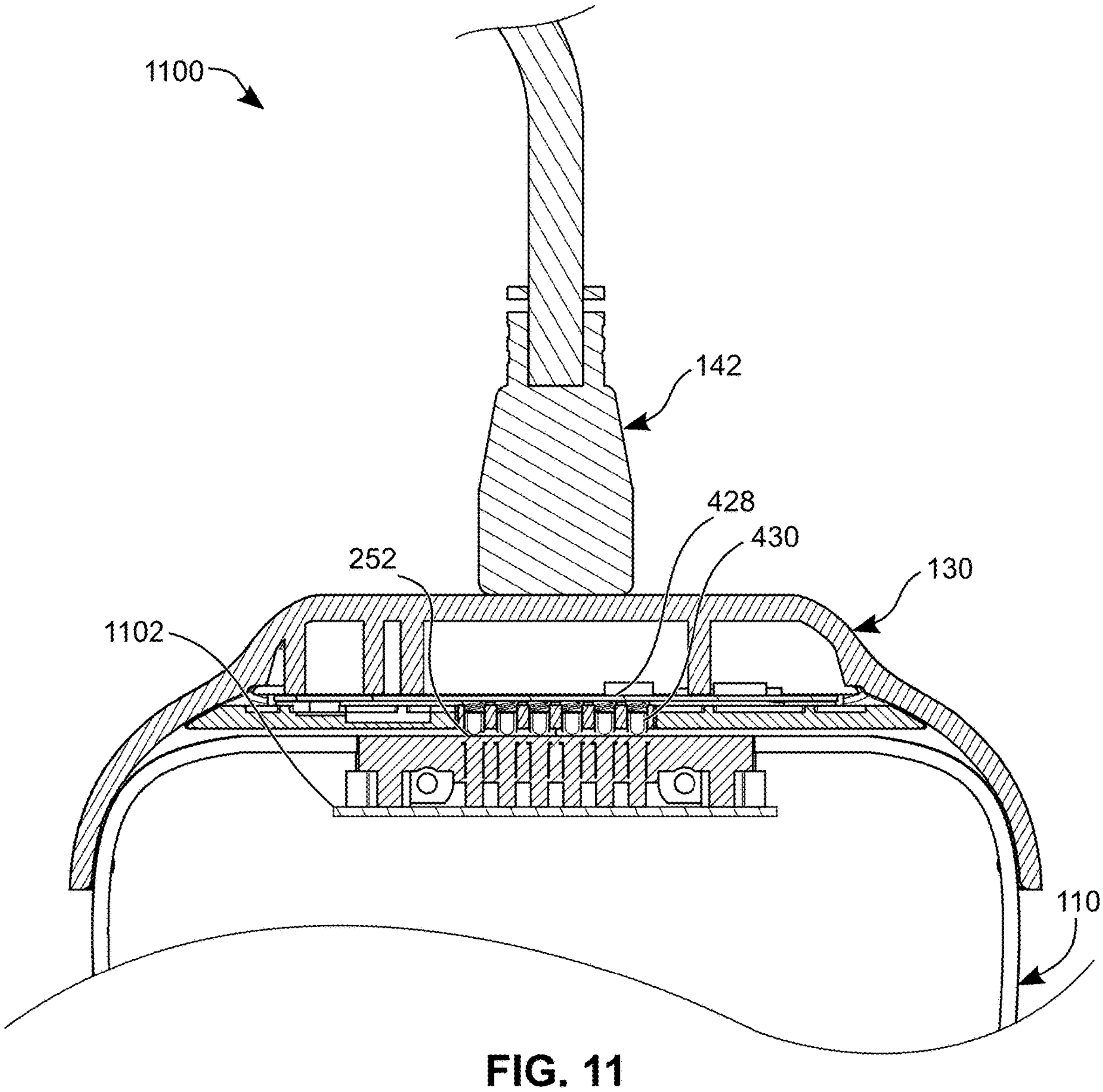
FIG. 11 is a partial cut-away and cross-sectional view of the ultrasound imaging system of FIG. 9 along line A-A shown in FIG. 9, in accordance with at least one embodiment of the present invention.

FIG. 11 illustrates a cross-sectional view through line A-A of FIG. 9 more specifically showing exemplary electronic connection points, in accordance with one aspect of the invention. Spring-loaded pins 430 extend from inner surface 428 on dual function charging and cooling unit 130. Target points 252 sit on top end 202 of ultrasound imaging apparatus and operably connect with integrated circuit 1102. Preferably spring-loaded pins are POGO™ pins from Everett Charles Technologies. In various embodiments, the spring-loaded pins and the target exposed pads should be chosen of a material that is suitable for immersion in a cleaning or disinfection solution.

In another alternative embodiment of the present invention, an electronic connection point between dual function charging and cooling unit 1202 and the ultrasound imaging device 1302 is wireless, thereby enabling the conveyance and supply of power from the dual function charging and cooling unit 1202 to the ultrasound imaging device 1302 without a wired connection of any type. This wireless connection is illustrated at 1200 in FIG. 12 and at 1300 in FIG. 13 (which figures are similar respectively, to FIG. 4 and FIG. 5, described above). To this end, behind inner surface 1208 of cap portion 1207, there is provided a wireless charger, including an induction coil (shown in another embodiment in FIG. 14). A second induction coil is provided in the ultrasound imaging device 1302 behind charging mat 1304 to enable the transmission of electrical energy through a either a magnetic or electrical field from the induction coil in wireless charger 1210 to receiving coil (behind charging mat 1304).

Figure 14:
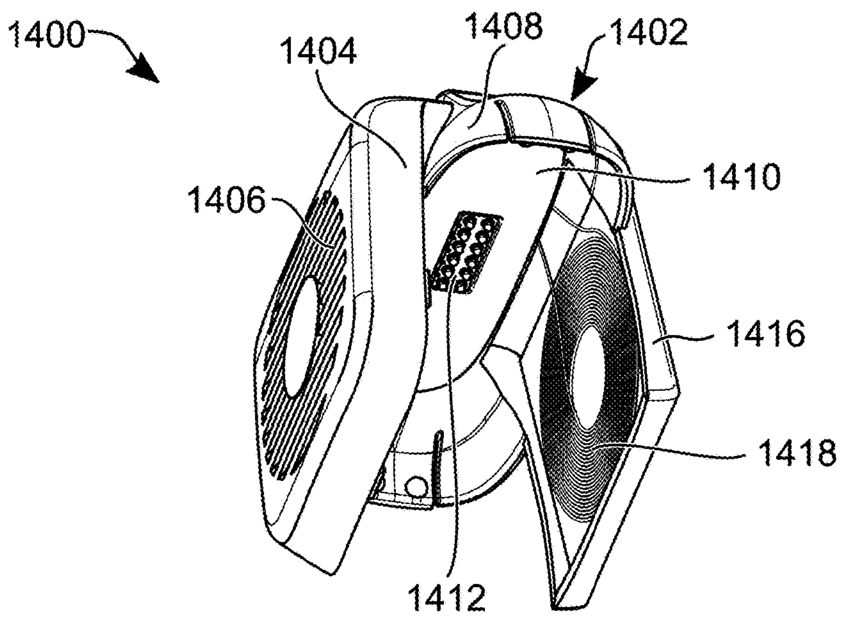
FIG. 14 shows a perspective view of a U-shaped dual function charging and cooling unit, in accordance with at least one embodiment of the present invention.
Figure 15:
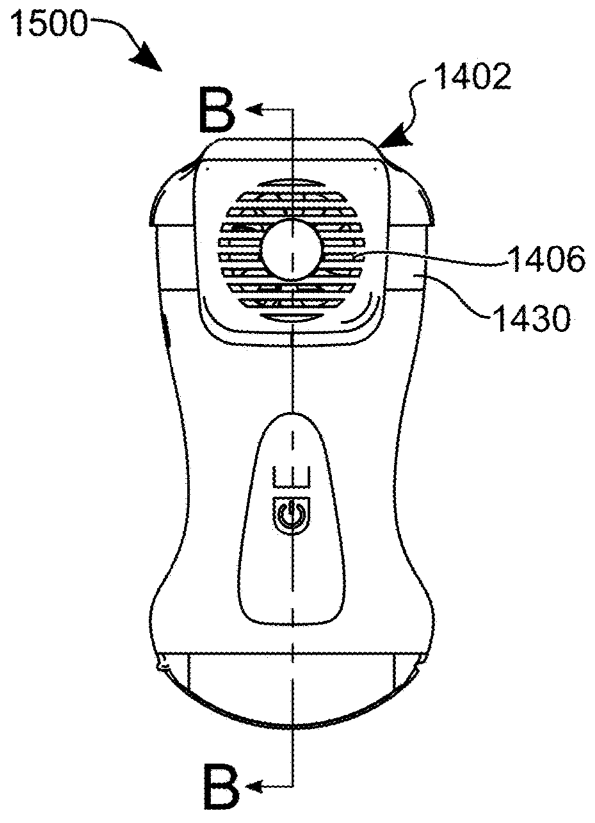
FIG. 15 shows a front view of the U-shaped dual function charging and cooling unit of FIG. 14, coupled to an ultrasound imaging apparatus, in accordance with at least one embodiment of the present invention.
Figure 16:
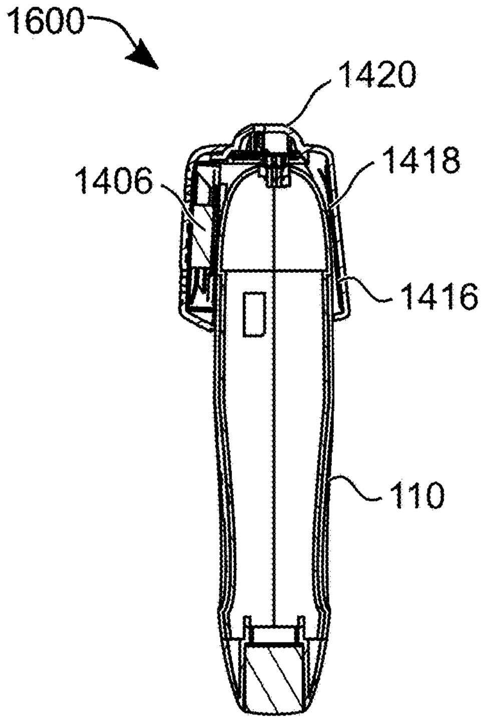
FIG. 16 shows a cross-sectional view of the U-shaped dual function charging and cooling unit of FIG. 15 through line B-B, including coupled ultrasound imaging apparatus, in accordance with at least one embodiment of the present invention.

An additional configuration of a dual function charging and cooling unit within the scope of the invention is illustrated in FIGS. 14-17. This configuration includes a second extension arm on the cap to house a larger induction coil for enhanced wireless charging capabilities (the first housing comprising the active cooling element, for example, a fan). FIG. 14 provides, at 1400, a U-shaped dual function charging and cooling unit 1402 comprising active cooling element housing 1404 (comprising active cooling element 140, shown as fan 1406) extending downwardly from the cap portion 1408 and induction coil housing 1416 (comprising induction coil 1418). When the dual function charging and cooling unit 1402 (specifically, cap portion 1408) is coupled over top end 202 of ultrasound imaging apparatus 110 (with surface 1410 mating with top of ultrasound imaging apparatus), both the active cooling element housing 1404 and the induction coil housing 1416 secure and hold active cooling element 140 directly over side surface 1430 (heat dissipator) of the ultrasound imaging apparatus. U-shaped dual function charging and cooling unit 1402 may be powered by an internal battery or by charging through a wired connection (for example through connection to a USB port within cap portion 1408). Spring-loaded pins are provided at 1412. FIG. 15 illustrates U-shaped dual function charging and cooling unit 1402 in place on ultrasound imaging device 110. FIG. 16 is a cross-sectional view through B-B of FIG. 15 and illustrates the orientation and configuration of each arm (1401 and 1416) of the U-shaped dual function charging and cooling unit 1402.

In some embodiments, the connection between ultrasound imaging apparatus 110 and dual function charging and cooling unit 130 is through a wireless, radio-wave based, communication interface such as a Bluetooth interface.

During operation, ultrasound imaging apparatus 110 may transmit ultrasound image or other data to a tertiary device for display or storage. For example, ultrasound imaging apparatus 110 may transmit data via a wired or wireless connection to a multi-use electronic display device to display an ultrasound image.

While various embodiments of the invention describe a removably corded conveyance of recharging power to battery 118 of ultrasound imaging apparatus 110, employing the dual function charging and cooling unit 130 as a power conduit, it is preferred, in other embodiments to convey such battery charging power via a separate internal battery within the dual function charging and cooling unit 130 thus enabling a fully cordless operation of the system. Such a separate internal battery within the dual function charging and cooling unit 130 may be rechargeable via a power cord as described herein or via wireless charging through a charging dock, surface or platform.

Within one aspect of the invention, the dual function charging and cooling unit is may be powered by in the ultrasound imaging device, or powered independently (for example, by an internal battery within the in the dual function charging and cooling unit. In some embodiments, the ultrasound imaging apparatus may be configured to not have a connector for supplying power to the dual function charging and cooling unit. For example, this may simplify design or manufacturing of the ultrasound imaging apparatus. Instead, the dual function charging and cooling unit may include an internal power source such as a battery. The battery may provide power to the dual function charging and cooling unit (as shown in FIG. 1) to help remove heat from ultrasound imaging apparatus. In various embodiments, the internal battery may be rechargeable or single-use. In various embodiments, the internal battery may be removable or non-removable. In various embodiments, the dual function charging and cooling unit may be provided with a switch that allows for the activation and/or deactivation of the active cooling element.

Various embodiments discussed herein may configure the ultrasound imaging apparatus 110 to be protected from ingress. As discussed, this may facilitate case of cleaning (e.g., allow for wiping with disinfection solution and/or allow for the ultrasound imaging apparatus 110 to be submersed in liquid). The embodiments may be configured to maintain this ingress protection given the disclosed electrical connectors that mate with electrical connectors from the cooling unit 130 (for example, spring-loaded pins and mating target points, neither of which offer significant contaminant ingress risks).

In some embodiments, the dual function charging and cooling unit 130 may receive power from ultrasound imaging apparatus 110 without the use of a conductor-based (e.g., wired) electrical connection. For example, various conventionally known or future-developed wireless power transfer techniques may be used provide power to dual function charging and cooling unit 130. For example, inductive coupling, capacitive coupling, and/or magnetodynamic coupling may be used to transfer power from ultrasound imaging apparatus 110 to the dual function charging and cooling unit 130 to power active cooling element 140.

Although the active cooling element 140 has generally been described herein as being provided in the form of fan 420, other types of active cooling element are possible. Various conventionally known or future developed active cooling elements may be used to remove heat from the ultrasound imaging apparatus 110. For example, a thermoelectric cooler or a refrigeration cycle-based heat pump may be used alone or in combination to provide active cooling.

As illustrated herein, the ultrasound imaging apparatus 110 is shown as being in the form of a wireless ultrasound scanner that may connect via wireless communication protocols to a suitable display for displaying the ultrasound image data generated from the scanner. However, the present embodiments can be practiced with ultrasound imaging apparatus of any types, whether wired or wireless. By providing a dual function charging and cooling unit 130 that either draws power from the ultrasound imaging apparatus 110 or is self-powered (as discussed above), the dual function charging and cooling unit 130 can provide the advantages of active cooling while still being cordless. In addition, within the scope of the invention, by providing an ultrasound imaging apparatus 110 which can draw power directly or indirectly from the dual function charging and cooling unit 130, ultrasound imaging apparatus 110 can operate longer, more efficiently and more safely for both the operator and patient due to charging and simultaneous cooling functionalities. This may allow for scanning of longer duration for ultrasound imaging apparatus 110 that is either wired or wireless.

In various embodiments, the ultrasound imaging apparatus 110 may be configured to control activation of a dual function charging and cooling unit 130 based on temperature sensors provided within the ultrasound imaging apparatus 110. For example, an ultrasound operator may wish to perform an ultrasound examination in a location with a high ambient temperature. The ultrasound operator may attach the dual function charging and cooling unit 130 to the ultrasound imaging apparatus 110 and begin scanning. When the dual function charging and cooling unit 130 is attached, an electrical connection may be formed, which may allow a processor within the ultrasound imaging apparatus 110 to detect the dual function charging and cooling unit's 130 presence and control power to it. The ultrasound imaging apparatus 110 may be provided with temperature sensor(s) that the processor may monitor. If the temperature exceeds a predetermined value, the processor may turn on dual function charging and cooling unit 130. When powered on, the active cooling element (e.g., a fan) may force air past a heat dissipating portion of the ultrasound imaging apparatus 110 and enhance the cooling beyond natural convection. This may allow the ultrasound operator to continue scanning in a situation where the temperature sensor may otherwise need to stop the ultrasound imaging apparatus 110 from scanning due to high temperatures. Furthermore, an operator can additionally charge and provide power to a portable ultrasound imaging apparatus from the dual function charging and cooling unit, directly or indirectly, without interruption of scanning.

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

C. Interpretation of Terms

Unless the context clearly requires otherwise, throughout the description and the

- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.
- Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

D. Claim Support

In one aspect of the invention, there is provided an ultrasound imaging system, comprising an ultrasound imaging apparatus operable to acquire ultrasound image data and comprising a power accepting interface; and a dual function charging and cooling unit configured to detachably couple to the ultrasound imaging apparatus; wherein the dual function charging and cooling unit comprises i) a power conveying element to convey power to the ultrasound imaging apparatus and ii) an active cooling element for removing heat from the ultrasound imaging apparatus.

In some embodiments, the power conveying element comprises a power port for mating with a detachable power cord, and an electronic assembly to power the ultrasound imaging apparatus, and wherein the power accepting interface accepts said power from the detachable power cord and electronic assembly, when the ultrasound imaging apparatus is coupled to the dual function charging and cooling unit.

In some embodiments, the power port is selected from the group consisting of a micro A Universal Serial Bus (USB), a micro B USB, a micro USB 3 and a USB C.

In some embodiments, the power conveying element comprises a battery and an electronic assembly to power the ultrasound imaging apparatus, and wherein the power accepting interface accepts said power from the battery, when the ultrasound imaging apparatus is coupled the dual function charging and cooling unit.

In some embodiments, the power accepting interface comprises a plurality of spring-loaded pins and power conveying element comprises a plurality of target mating receptacles.

In some embodiments, the power conveying element and the power accepting interface each comprise an induction coil for wireless charging.

In some embodiments, the ultrasound imaging apparatus further comprises at least one sensor for detecting when the cooling unit is attached. In some embodiments, the sensor is magnetic. In some embodiments, the sensor comprises at least a portion of a resistor voltage divider network.

In some embodiments, the dual function charging and cooling unit receives power from the ultrasound imaging apparatus. In some embodiment, the dual function charging and cooling unit further comprises a battery for powering the active cooling element.

In some embodiments, the ultrasound imaging system of claim 1, wherein the ultrasound imaging apparatus comprises an external surface and the active cooling element comprises a fan, and wherein said fan is configured to direct air onto or from said external surface.

In some embodiments, the dual function charging and cooling unit comprises at least one fastener to perform the detachable coupling.

In another aspect of the invention, there is provided a dual function charging and cooling unit for an ultrasound imaging apparatus, the cooling unit comprising a housing comprising a fastener for detachably coupling the dual function charging and cooling unit to the ultrasound imaging apparatus; a power conveying element to convey power to the ultrasound imaging apparatus, when coupled; and an active cooling element enclosed in the housing and configured to remove heat from the ultrasound imaging apparatus, when coupled.

In another aspect of the invention, there is provided an ultrasound imaging system, comprising an ultrasound imaging apparatus operable to acquire ultrasound image data and comprising an apparatus electronic connection point; and a dual function charging and cooling unit configured to detachably couple to the ultrasound imaging apparatus; wherein the dual function charging and cooling unit comprises i) a power source port for mating with a detachable power cord, to power the ultrasound imaging apparatus; ii) a unit electronic connection point for mating with the apparatus electronic connection point, to convey power between the detachable powering cord and the ultrasound imaging apparatus and iii) an active cooling element for removing heat from the ultrasound imaging apparatus.

What is claimed is:

1. An ultrasound imaging system, comprising:

an ultrasound imaging apparatus;

a dual function unit operable with the ultrasound imaging apparatus; and a power and data conveyance cord configured to detachably couple, at one end, to the ultrasound imaging apparatus, via the dual function unit, and to detachably couple, at another end, to a multi-use display device;

wherein the power and data conveyance cord, when coupled to both the ultrasound imaging apparatus and the multi-use display device, enables the conveyance of power to the ultrasound imaging apparatus and enables the transfer of ultrasound image data between the ultrasound imaging apparatus and the multi-use display device.

2. The ultrasound imaging system of claim 1 wherein ultrasound image data is acquired by the ultrasound imaging apparatus.

3. The ultrasound imaging system of claim 1 wherein the dual function unit comprises a power conveying element and a power port for mating with the power and data conveyance cord.

4. The ultrasound imaging system of claim 3 wherein the power port is selected from the group consisting of a micro A Universal Serial Bus (USB), a micro-B USB, a micro-USB 3 and a USB C.

5. The ultrasound imaging system of claim 3 wherein power conveying element comprises a plurality of target mating receptacles which are matable with a plurality of spring-loaded pins on the ultrasound imaging apparatus, when coupled.

6. The ultrasound imaging system of claim 3 wherein power conveying element comprises an induction coil for wireless charging.

7. The ultrasound imaging system of claim 1, wherein the power and data conveyance cord comprises, at least one end, a port selected from the group consisting of USB, USB mini or USB micro male/USB C for connection to a female port.

8. The ultrasound imaging system of claim 1, wherein the multi-use display device comprises a display for displaying the ultrasound image data.

9. The ultrasound imaging system of claim 1, wherein the multi-use display device comprises storage for the ultrasound image data.

10. The ultrasound imaging system of claim 1, wherein the multi-use display device receives ultrasound image data from the ultrasound imaging apparatus alternatively through the power and data conveyance cord and wirelessly, via a wireless connection between and the ultrasound imaging apparatus and the multi-use display device.

11. The ultrasound imaging system of claim 10 wherein the multi-use display device and the ultrasound imaging apparatus exchange ultrasound image data through the wireless connection therebetween and the ultrasound imaging apparatus receives power through the power and data conveyance cord.

12. The ultrasound imaging system of claim 1, wherein the ultrasound imaging apparatus is handheld.

13. The ultrasound imaging system of claim 1, wherein the multi-use display device is a device comprising a processor communicatively operable with a screen interface, selected from the group consisting of laptop computer, a tablet computer, a desktop computer, a smart phone, a smart watch, spectacles with a built-in display, a television, and a bespoke display.

14. A method of data and power connection between an ultrasound imaging apparatus and a multi-use display device comprises:

providing a dual function unit operable with the ultrasound imaging apparatus;

providing a power and data conveyance cord configured to detachably couple, at one end, to the ultrasound imaging apparatus, via the dual function unit, and to detachably couple, at another end, to a multi-use display device;

conveying power to the ultrasound imaging apparatus when the power and data conveyance cord is coupled to both the ultrasound imaging apparatus and the multi-use display device; and transferring ultrasound image data between the ultrasound imaging apparatus and the multi-use display device.

15. The method of claim 14 wherein ultrasound image data is acquired by the ultrasound imaging apparatus.

16. The method of claim 14, wherein the power and data conveyance cord comprises, at least one end, a port selected from the group consisting of USB, USB mini or USB micro male/USB C for connection to a female port.

17. The method of claim 14 wherein the multi-use display device comprises a display for displaying the ultrasound image data.

18. The method of claim 14 wherein the multi-use display device comprises storage for the ultrasound image data.

19. The method of claim 14, wherein the multi-use display device receives ultrasound image data from the ultrasound imaging apparatus alternatively through the power and data conveyance cord and wirelessly, via a wireless connection between and the ultrasound imaging apparatus and the multi-use display device.

* * * * *